(12) United States Patent
Broggini et al.

(10) Patent No.: US 7,189,840 B2
(45) Date of Patent: Mar. 13, 2007

(54) ONCOSUPPRESSIVE GENE

(75) Inventors: Massimo Broggini, Bresso (IT);
Maurizio D'Incalci, Bresso (IT)

(73) Assignee: Novuspharma S.p.A. (IT)

( * ) Notice: Subject to any disclaimer, the term of this patent is extended or adjusted under 35 U.S.C. 154(b) by 0 days.

(21) Appl. No.: 10/483,241

(22) PCT Filed: Jul. 9, 2002

(86) PCT No.: PCT/EP02/07625

§ 371 (c)(1),
(2), (4) Date: Jul. 14, 2004

(87) PCT Pub. No.: WO03/006498

PCT Pub. Date: Jan. 23, 2003

(65) Prior Publication Data

US 2004/0259251 A1    Dec. 23, 2004

(30) Foreign Application Priority Data

Jul. 10, 2001    (IT) .......................... MI2001A1465

(51) Int. Cl.
*C07H 21/04*    (2006.01)
*C12N 15/00*    (2006.01)

(52) U.S. Cl. .................. 536/24.1; 435/320.1; 536/23.1

(58) Field of Classification Search ..................... None
See application file for complete search history.

(56) References Cited

FOREIGN PATENT DOCUMENTS

WO    WO 01 75067 A    10/2001
WO    WO 02/28999 A2   4/2002

OTHER PUBLICATIONS

Nagase et al. Prediction of the Coding Sequences of Unidentified Human Genes. VI. The Coding Sequences of 80 New Genes (KIAA0201-KIAA0280) Deduced by Analysis of cDNA Clones from Cell Line KG-1 and Brain. DNA Research, vol. 3, pp. 321-329, 1996.*
GenBank Accession No. D87434.1, Nov. 8, 1996.*
Pietrzkowski et al. Characterization of an enhancer-like structure in the promoter region of the proliferating cell nuclear antigen (PCNA) gene. Exp Cell Res. vol. 193, No. 2, pp. 283-290, Apr. 1991.*
Chan et al. Promoter analysis of the nuclear gene encoding the chloroplast glyceraldehyde-3-phosphate dehydrogenase B subunit of *Arabidopsis thaliana*. Plant Mol Biol. vol. 46, No. 2, pp. 131-141, May 2001.*
El-Deiry et al. Definition of a consensus binding site for p53. Nat Genet. vol. 1, No. 1, pp. 45-49, Apr. 1992.*
Omilli et al. Sequences involved in initiation of simian virus 40 late transcription in the absence of T antigen. Mol Cell Biol. vol. 6, No. 6, pp. 1875-1885, Jun. 1986.*
GenBank Accession No. AL133445, GI: 13897486, publicly available Apr. 2001.*
Database EMBL, Online, Feb. 13, 2002, Drmanac R.T., "DNA encoding human diagnostic protein #23497", retrieved from EBI Database accession No. AAS87693 XP002232526.
Database EMBL, Online, Aug. 14, 2002, Beazer-Barclay et al., "Human cDNA differentially expressed in granulocytic cells #298", retrieved from EBI Database accession No. ABK83727 XP002232527.
Database EMBL, Online, Jul. 2, 2001, Lee et al., "Human late stage ovarian tumour polynucleotide marker 8", retrieved from EBI Database accession No. AAF98711 XP002232528.
Database EMBL, Online, Nov. 9, 1996, Ohara et al., "Human mRNA for KIAA0247 gene", Database accession No. D87434 XP002232529.
Database EMBL, Online,EBI, EST, Organ: mammary, tissue: tumor biopsy sample, Feb. 15, 2000, Strausberg R.: "Mus musculus cDNA clone Image: 2648685 5', mRNA", Database accession No. AW412392 XP002243000.
Database EMBL, Online, EBI, Feb. 2, 2001, Rosen, C.A., "Human secreted protein cDNA #6", Database accession No. AAC59340 XP002243001.
Funk et al., "A transcriptionally active DNA-binding site for human P53 protein complexes", Molecular and Cellular Biology, Washington, DC, vol. 12, No. 6, Jun. 1, 1992, pp. 2866-2871, XP000676472.
De Laurenzi et al., "Evolution of functions within the p53/p63/p73 family" Annals of the New York Academy of Sciences, vol. 926, Dec. 2000, pp. 90-100 XP009011712.
Ng Shu-Wing et al., "Analysis of p73 in human borderline and invasive ovarian tumor", Oncogene, vol. 19, No. 15, Apr. 6, 2000, pp. 1885-1890 XP009011716.
Pestell et al., "Characterisation of the P53 status, BCL-2 expression and radiation . . . ", International Journal of Cancer, vol. 77, No. 6, pp. 913-918 XP002242999.

* cited by examiner

*Primary Examiner*—Celine Qian
*Assistant Examiner*—Jennifer Dunston
(74) *Attorney, Agent, or Firm*—Lerner, David, Littenberg, Krumholz & Mentlik, LLP

(57) ABSTRACT

Isolation and characterization of an oncosuppressive gene which is involved in the apoptotic process and is regulated by p53 ad p73, polypeptide thereby encoded, sequences involved in gene regulation and genetic constructs thereof.

4 Claims, 13 Drawing Sheets

Control
(A2780/pCDNA3)

A2780/cDNA

ONCOSUPPRESSIVE GENE

CROSS REFERENCE TO RELATED APPLICATION

This application is a 35 U.S.C. § 371 National Phase Entry Application from PCT/EP02/07625, filed Jul. 9, 2002, and designating the U.S.

The present invention regards the isolation and characterization of a novel gene which is involved in programmed cell-death (apoptosis) and has oncosuppressive activity. The gene is regulated by p53 and p73, which are known to activate the transcription of genes involved in cell-cycle block and apoptosis. p73 and p53 have homologous sequences, especially in the central region including the DNA-binding domain, and share a common pattern of gene-activation. However, their oncosuppressive activities, in particular the pro-apoptotic effects, are not completely clarified. Therefore the search of genes activated by p53 and p73 attracts a great scientific and applicative interest.

PRIOR ART

Nagase et al., DNA Research 3, 321–329 (1996), reports the sequencing of human cDNA clones obtained from a library of human cDNAs, and the predicted coding sequences of 80 new genes (KIAA0201 to KIAA0280) deduced by analysis of cDNA clones. The coding sequence named KIAA0247 is present in the gene isolated according to this invention. The referenced publication does not contain information as to the structure and function of the gene.

WO01/18542 lists a huge number of cDNA sequences identified by subtraction library construction, which are overexpressed in ovarian tumor cells and hence proposed for use as ovarian cancer markers. Sequence n. 1.18 shows high homology with the coding sequence of the present gene.

DESCRIPTION OF INVENTION

In differential-display experiments with human ovarian carcinoma cells A2780, a cDNA fragment whose expression increased after treating the cells with a synthetic derivative of distamycin A was identified. This compound is known to interact with the DNA minor groove.

The same effect was observed with cytotoxic compounds differing from distamycin A by their mechanism of action, such as cisplatin, taxol, doxorubicin and fluorouracil; obtaining in each case an increased production of the same fragment.

To verify whether the increase was mediated by p53, the effects of antitumnor drugs were evaluated in isogenic model-systems differing for p53 expression. An increased transcription of the isolated cDNA could not be observed in cells where the p53 gene had been inactivated, suggesting that the activity of the gene under investigation is regulated by p53.

The complete cDNA containing the isolated fragment was then isolated from a cDNA-library and entirely sequenced. It has 5338 base pairs (SEQ ID N. 1) and codes for a protein of 303 amino acids (SEQ ID N. 2). The coding region spans nucleotides 269 to 1177 (1180, including the stop codon "tga"), while nucleotides 1180–5338, which form the non-translated 3' region (SEQ ID N. 3), are involved in the regulation of protein synthesis by controlling the stability of the corresponding transcript.

In a first embodiment the invention is directed to a DNA molecule having sequence SEQ ID No. 1. In a further embodiment the invention provides SEQ ID N. 3, which is the sequence complementary to the non-translated mRNA region involved in the regulation of protein synthesis.

Included within the scope of the invention are also nucleic acid molecules, their stable analogs or mimetics, such as PNA (Peptide Nucleic Acid) molecules, or other derivatives thereof that do not undergo in vivo degradation or biotransformation, which can hybridize to the DNA molecule of SEQ ID No. 3, or to a complementary sequence thereof. Such products can be used to modulate the function of the regulatory sequence contained in the transcript of the isolated gene. As herein used, the term "hybridization" may refer to stringent or non-stringent conditions. These can be easily determined by anyone skilled in the art following known protocols (see for example Sambrook, "Molecular Cloning, A Laboratory Manual", Cold Spring Harbor Laboratory, N.Y. (1989), or Ausbel, "Current Protocols In Molecular Biology", Green Publishing Associates and Wiley Interscience, N.Y. (1989)).

The protein encoded by the complete cDNA was biochemically characterized. It showed a molecular weight, calculated by SDS-PAGE, of 30–35 kDa, consistent with the number of amino acids (303) deducible from the sequence. To determine its cellular location, fusion proteins were prepared from constructs combining the isolated c-DNA sequence with sequences coding for proteins or protein fragments detectable by microscopy, such as HA, FLAG or GFP. In these experiments the cells were transiently transfected and examined at different times. The expression product bearing the GFP protein was found to locate within cell vesicles and membranes. The same location was observed in different human and murine cell lines. Further, morphologic changes following gene overexpression were evaluated in transiently transfected cells. Several cytoplasmic vacuoles were present in cells transfected with the GFP-cDNA construct. In some cases the cell membranes appeared disrupted and the vacuole content was extracellularly released. The same effects were previously reported for apoptotic cell lines other than those of type II (where nuclear fragmentation occurs).

According to a further aspect, the invention is directed to the polypeptide SEQ ID N. 2 and to its DNA coding sequence SEQ ID N. 4. Included are also sequence variants of the polypeptide SEQ ID N. 2, due to substitution, addition or deletion of one or more amino acids, provided that its specific functions are maintained. As to the deletion variants, peptides generated by repeated deletions at the N-terminus of SEQ ID N. 2 showed an activity similar to that of the parent polypeptide. In particular, (poly)peptides 12-303, 23–303, 35–303, 49–303, 60–303 and 74–303 (referred to nucleotide positions in SEQ ID N. 2), which were found to maintain the same oncosoppressive activity as the parent polypeptide, represent a further object of the invention.

Using the information available with the fall-length cDNA, the structure of the human oncosuppressive gene (DRAGO) was molecularly characterized. It consists of 6 exons, the first of which (188 bp) forming the non-translated 5' region. Exons 2,3,4 and 5 (201, 198, 140 and 427 bp respectively) correspond to the coding region which contains the first 26 bases of exon 6 (4184 bp) and additionally the entire non-translated 3', region. Interestingly, the gene presents two large introns (45–50 kb) between exons 1–2 and 2–3, respectively. The presence of such introns, and of the large untranslated region as well, implies a strong gene regulation. Starting from a 10735 bp region located upstream of the first exon (SEQ ID N. 5), a 3761 bp fragment (SEQ ID N. 6), consisting of the first intron, the first exon and a sequence portion contiguous to exon-1 5'-end, was isolated. This fragment was functionally linked to a reporter gene (luciferase) to determine its transcription promoter activity. In p53-defective cells, a sustained transcription of the reporter gene could be detected. In cells where p53 functionality had been restored by co-transfection of a vector carrying the p53 gene under the control of a strong viral promoter, the promoter activity of the 3761 fragment was two-fold increased. This result is consistent with the experiments conducted in isogenic p53$^+$ or p53$^-$ model-systems. The observed p53 regulation is similar to that of other p53-responsive promoters such as the p21-gene promoter.

An even stronger promoter activity in response to p73 and p53 was observed with fragments of the 3761 bp sequence. In experiments where cells were co-transfected with DNA fragments—SEQ ID. No. 9 to 15—subcloned upstream of the luciferase gene and with either p73- or p53-encoding plasmids, a high expression of the reporter was found.

Sequences SEQ ID N. 5–6 and 9–15, which are endowed with transcription promoter activity responsive to p53 and p73, are embodiments of this invention. They can be used in the preparation of gene constructs and vectors useful for the study of oncosuppressive-gene expression. In particular these sequences, as well as the untranslated regulatory sequence of SEQ ID N. 3, can be used for the screening of compounds that modulate the expression of the oncosuppressive product. In a typical assay, the candidate compound is incubated with cells transfected with the regulatory sequences operatively linked to a suitable reporter gene, and then the ability of the e compound to modulate the expression of the reporter gene and/or to modify particular cell functions or properties, such as their growth in response to particular stimuli, is determined. Moreover, animals transgenic for the same sequences can be produced. In a further application, animal models carrying particular tumors can be used to study the ability of candidate compounds to modulate the expression of the oncosuppressive gene.

The murine oncosuppressive gene was also cloned and resulted highly homologous to the human gene, with a nucleotide (SEQ ID N. 7) and amino acid (SEQ ID N. 8) identity of 87% and 88%, respectively.

The identification of murine gene sequences enables the preparation of knock-out mice. A suitable strategy can be summarized as follows. Initially, a region of the gene of approx. 6–7 kb, preferably containing the exons 3–5, after insertion in a suitable vector, is partially replaced by a gene conferring antibiotic resistance, such as the neomycin-resistance gene, which, besides functioning as selection marker, causes inactivation of the oncosuppressive gene by interrupting its transcription.

ES cells are then transfected with the recombinant construct and only those keeping viable and growing in a medium added with the antibiotic are selected. The positive clones are then identified by PCR and Southern blot and introduced into blastocysts by microinjection. The thus generated chimera mice are initially heterozygous (−/+) and then, after breeding, homozygous (−/−) for the inactivated gene.

EXAMPLES

Example 1

Isolation and Characterization of the Human cDNA

Human ovary carcinoma A2780 cells were treated for 1 hour with an antitumor derivative of distamycin-A at its 50% growth-inhibiting concentration; at the end of the treatment and after 6 and 24 hours the total RNA was isolated by column extraction (SVTotal RNA, Promega Italia) and reverse-transcribed using poly-T primers as indicated in the differential-display kit (GenHunter). The fragments thus obtained were separated on denaturing polyacrylamide gel and detected by autoradiography. The bands whose intensity differed from controls were isolated and purified. One of them (fragment 1), after purification and $^{32}$P-labeling (rediprime kit, Amersham), was used as probe in Northern Blot experiments. The RNA from the same cells was separated on agarose gel, transferred onto nylon membrane and hybridized with the probe.

To isolate the complete cDNA containing fragment 1, a cDNA library

Human ovary carcinoma A2780 cells were treated for 1 hour with an prepared from human fibroblasts using λgt10 vector was hybridized with the probe (see "Molecular Cloning, A Laboratory Manual", Cold Spring Harbor Laboratory, N.Y. (1989), or Ausbel, "Current Protocols In Molecular Biology", Green Publishing Associates and Wiley Interscience, N.Y. (1989)). The positive clones were isolated, sequenced and the full-length cDNA (5338 bp) was cloned in pBluescript vector (Stratagene). The coding region results comprised between nucleotides 269 and 1177 (1180 including the stop codon "tga") whereas the remaining 4158 nucleotides form the non-translated 3' region.

Example 2

Analysis of cDNA Expression in Cells Treated with Different Cytotoxic Agents

PCR experiments using oligonucleotides derived from the isolated cDNA evidenced an increase of mRNA production in cells treated with different antitumor compounds other than distamycin and having a different mechanism of action with respect to the latter, such as cisplatin and taxol, which cause DNA damage and microtubule stabilization, respectively.

Figure 1:
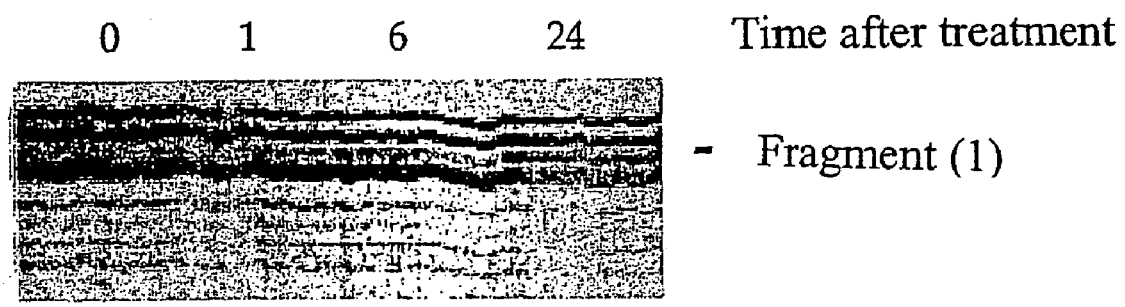
FIG. 1. Differential display analysis of gene expression in A2780 cells untreated or treated with a distamycin derivative for 1 hour. The RNA was extracted 1, 6 or 24 hours after treatment.
Figure 2:
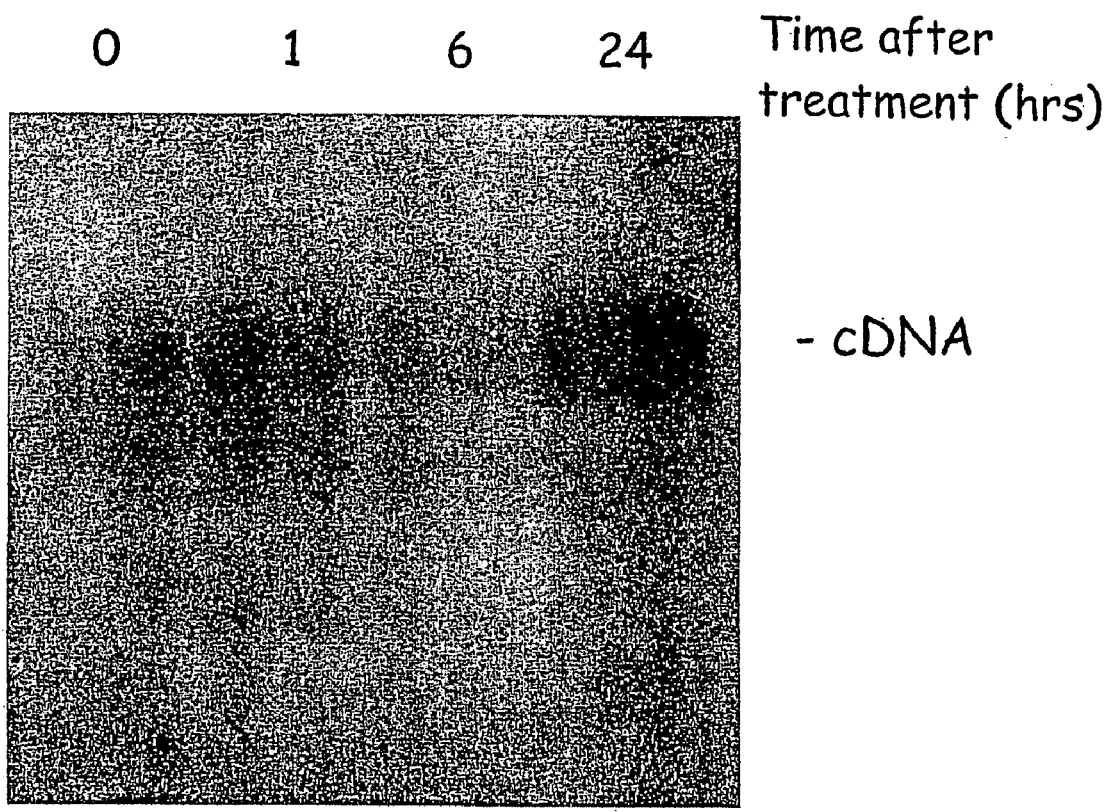
FIG. 2. Northern blot confirming the increased expression of fragment 1 mRNA (FIG. 1).
Figure 3:
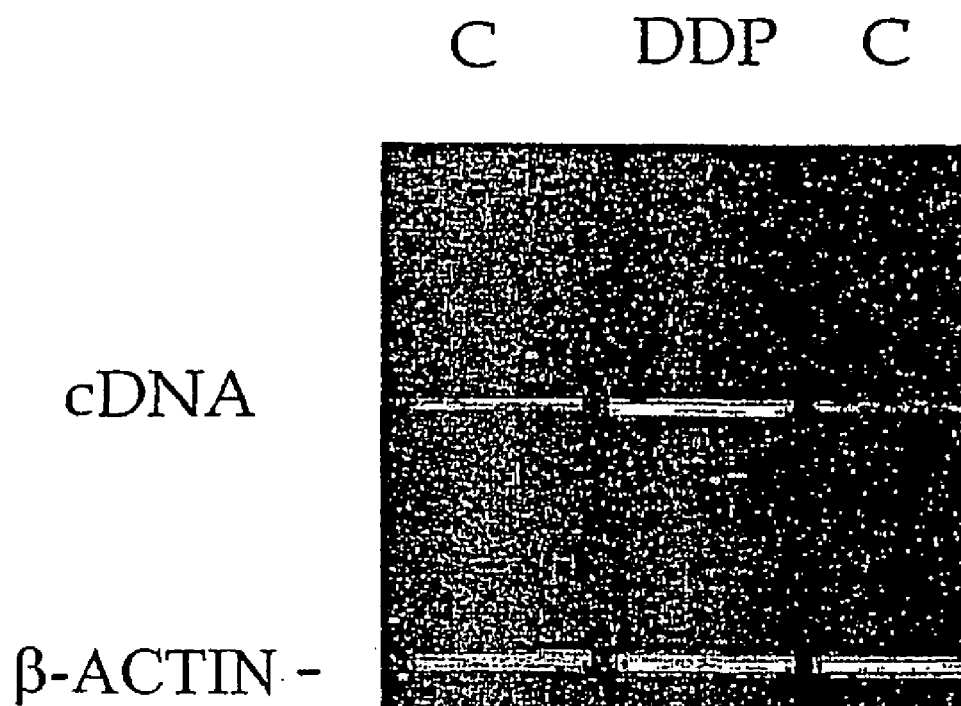
FIG. 3. RT-PCR analysis of the isolated-cDNA expression in control cells (C) and in cells treated with cisplatin (DDP).

Cells A2780 were treated with taxol and cisplatin (DDP) and the RNA was extracted before and 24 hours after the treatment. The amount of specific mRNA was determined by PCR following reverse-transcription of the total RNA (1 µg) with primers derived from the coding region of fragment 1 (5'-ctcgagtgccatggcaggatagcacc [SEQ ID NO: 17] and 5'-tctagatcatgcttctttcaacagtg [SEQ ID NO: 18]), according to the protocol supplied in the RNA-PCR kit (Perkin Elmer). The amplified fragment (923 bp) was separated on agarose gel. A fragment of beta-actin gene was used as internal control. FIG. 3 shows the results obtained treating the cells with cisplatin (DDP): the band associated with the isolated gene is more intense than that of control cells (C) in conditions in which the levels of beta-actin gene are comparable in the two groups. Similar results were obtained using taxol and other antitumor drugs.

Example 3

Protein Characterization and Intracellular Location

Figure 4:
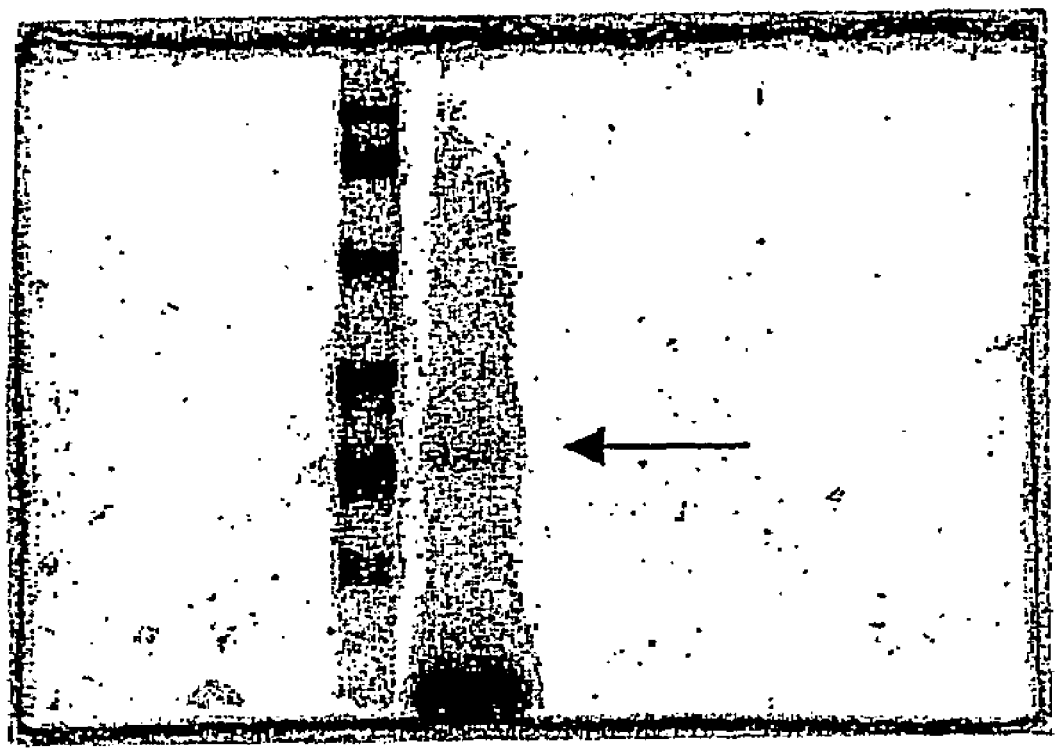
FIG. 4. SDS PAGE—the protein produced in vitro from the isolated cDNA is indicated by an arrow. Gel stained with Coomassie Blue.

Using the isolated full-length cDNA as template, a polypeptide was produced (Promega TNT express kit) with an apparent molecular weight, calculated by SDS-PAGE, of 30–35 kDa (FIG. 4). This mol weight is consistent with the structure of the polypeptide and with the number of amino acids (303) deducible from its sequence (SEQ ID N. 2).

Transient transfection experiments were conducted to determine the intracellular location of the polypeptide. To this end, the latter was fused to proteins or protein fragments such as HA or FLAG, which can be detected by microscopy using fluorescent antibodies, or GFP, which is an intrinsically fluorescent protein. In these experiments the cells were analyzed 24 and 48 hrs after transfection with different constructs. Using a GFP-construct, the polypeptide was found to localize within cellular vesicles and membranous structures. Under the same conditions, as expected, GFP alone was uniformly located within the cell. The same effects were observed in different human and murine cell lines.

Transient transfection experiments were also conducted to assess morphologic modifications occurring 24 and 48 hrs after gene overexpression. Cells transiently transfected with a GFP construct showed in all cases the presence of several cytoplasmic vacuoles, less frequently the membrane appeared disrupted and the vacuole content released in the extracellular areas. Transfection with GFP alone was not associated with any evident morphologic alteration.

Example 4

Effects of Gene Overexpression in Eukaryotic Cells

The effects of gene overexpression were evaluated in cells carrying constructs in which the isolated cDNA was functionally linked to a strong viral promoter.

Figure 5:
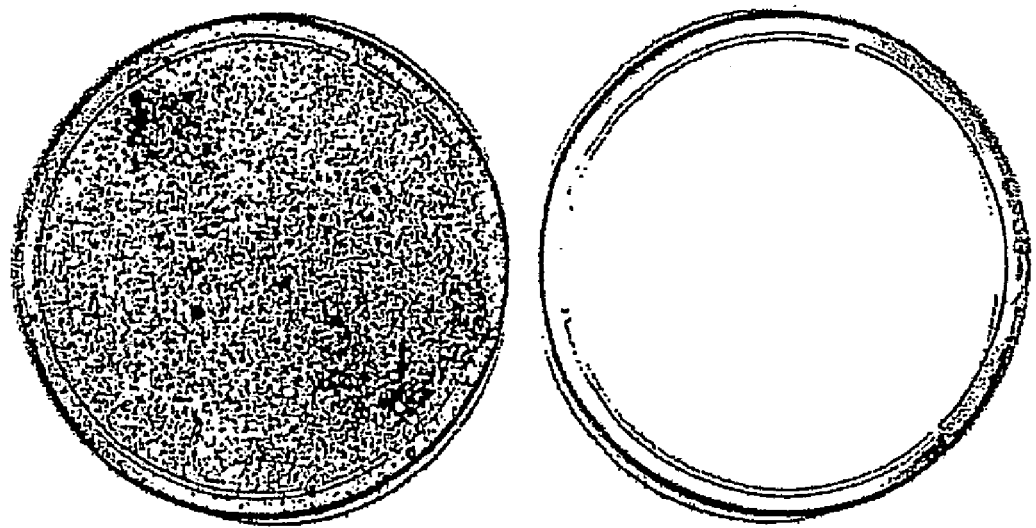
FIG. 5. Staining of A2780 colonies recovered after transfection with a control vector (pCDNA3) or with a vector containing the isolated cDNA.

The complete cDNA (5338 bp) and the coding region (nucleotides 1–1180) were used for vector assembly. The two sequences were excised from pBS plasmid (Stratagene) and inserted into pCDNA3 (Invitrogen), pCDNA3-HA and pCDNA3-FLAG expression vectors. These two latter were prepared from pCDNA3 by insertion of the HA and FLAG coding sequences. The coding portion of the isolated cDNA was amplified by PCR (primers: 5'-ctcgagtgcatggcaggatag-cacc [SEQ ID NO: 19] and 5'-tctagatcatgcttctttcaacagtg [SEQ ID NO: 18]) and sub-cloned in frame with the HA and FLAG sequences. Similar constructs were prepared from GFP (green fluorescent protein). In this case, the coding sequence of the isolated cDNA was subcloned in frame with the GFP cDNA in a pEGFP-C1 vector (Clontech). Each construct was automatically sequenced to verify its correct assembly and transfected into A2780 cells by calcium phosphate precipitation, according to the following procedure. 5–10 micrograms of plasmidic DNA were mixed with calcium chloride and phosphate buffer to form fine calcium phosphate precipitates, and this mixture was applied to a cell culture (70% confluence) for a period of 12–16 hrs. The cells were rinsed with PBS, rested for 48 hrs, counted and plated (5000 cells/10 cm plate) in a culture medium added with neomycin. 15 days later the culture medium was removed and the colonies dyed with crystal violet, washed and photographed. FIG. 5 shows the photograph of a plate in which A2780 cells were transfected with the isolated cDNA or with vector pCDNA3 alone. No colonies could be detected in cDNA-bearing cells, whereas several colonies were present in the culture treated with vector alone. The overexpression of the complete cDNA (5338 bp) or its 1180 bp fragment (coding region) prevented colony formation. This effect was observed in A2780 cells (ovary carcinoma), SaoS2 and U2OS lines (human osteosarcoma), and 3T3 lines (murine fibroblasts). Failure to isolate stable clones was due to the strong growth-suppressing effect following gene-overexpression.

Example 5

Role of p53 in Gene Activation

Figure 6:
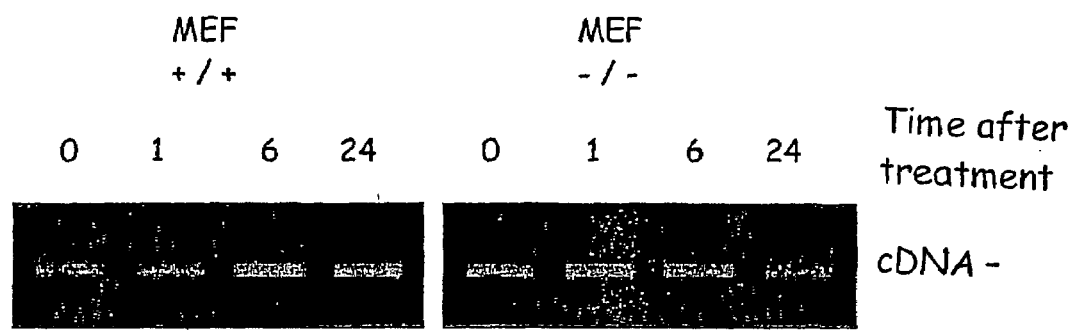
FIG. 6. RT-PCR analysis of the isolated-cDNA expression in murine embryonic fibroblasts from wild-type mice (+/+) or p53 (−/−) knock-out mice, treated or not with the distamycin derivative for 1 hour. The RNA was extracted 1, 6 or 24 hours after treatment.
Figure 7:
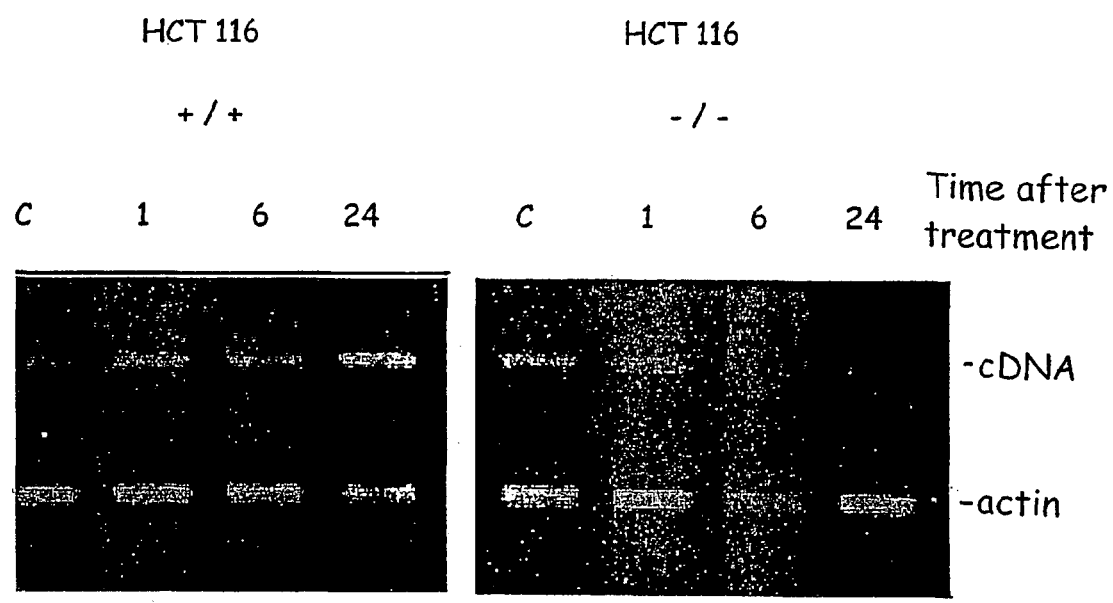
FIG. 7. RT-PCR analysis of isolated-cDNA expression in HCT116 cells expressing wild-type. p53 (+/+) or in HCT116 cells p53-inactivated by homologous recombination (−/−), treated or not (Controls) with the. distamycin-A derivative for 1 hour. The RNA was extracted 1, 6 or 24 hours after treatment.
Figure 8:
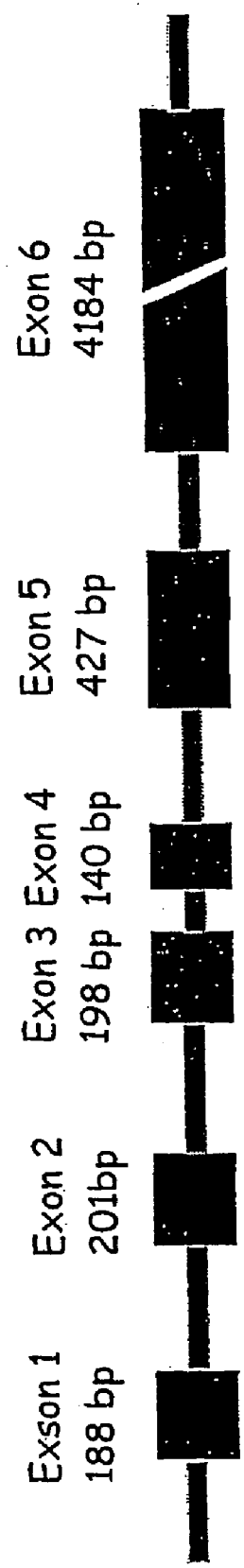
FIG. 8. Molecular structure of the gene, indicating the number of base pairs of each exon.

To ascertain whether the activity of the gene was mediated by p53, the effects of antitumor drugs in isogenic models with different p53 expression were examined. No expression was found in embryonic fibroblasts from p53 knock-out mice (FIG. 6). In these experiments, fibroblasts from wild-type and p53 knock-out mice were treated with a distamycin derivative for 1 hour. The RNA isolated 1, 6 and 24 hours after the treatment was used to amplify a cDNA containing the coding portion of the murine gene (primers: 5'-ctcgagt-gccatggcaggatagcacc [SEQ ID NO: 17] and 5'-tctagatcatgct-tctttcaacagtg [SEQ ID NO: 18]). The antitumor compound failed to induce gene expression in a HCT116 clone where p53 had been inactivated by homologous recombination (HCT116 p53 −/−); in contrast, gene expression was observed in the parental cell line (FIG. 7). The same conditions as in the experiments with embryonic fibroblasts were used. These results demonstrate that p53 is necessary for gene activation.

Example 6

Molecular Characterization of the Human Gene

A pCYPAC2-subcloned PAC RPCI1 genomic library from the UK Human Genome Mapping Project Resource Center was used (Hinxton, UK). This library was established from the blood of a healthy subject and consisted of approx. 120000 clones spotted in duplicate on 7 membrane filters (22.2 ×22.2 cm). A 5'-fragment (160bp) generated by PCR (primers: 5'-ctcgagtgccatggcaggatagcacc [SEQ ID NO:17] and 5'-tctagatcatgcttctttcaacagtg [SEQ ID NO: 18]) was used as hybridization probe. The latter was $^{32}$P-labeled and incubated with the filters for 16 hrs. After extensive washing, the filters were exposed to an autoradiographic film. Two positive clones (92D20 and 67A24) were identified and the genomic DNA of one of them was partially sequenced (terminal regions). Using sequence information available from a database, the structure of the gene was defined.

Example 7

Role of p53 in Gene Transcription

The region (10735 bp—SEQ ID N. 5) located upstream of the first exon was isolated from one PAC clone. A portion of it (3761 bp), containing the first intron (partially), the first exon and a region adjacent to the 5'-end of exon 1, was sub-cloned in pGL2 vector (Promega) upstream of the luciferase gene. A significant transcription of the reporter gene was detected with a luninometer 48 hrs after transfection of semi-confluent p53$^-$ cells with the construct (10 μg). Cells transfected with pGL2 vector alone (without the 3761 bp fragment) were used as the control.

Figure 9:
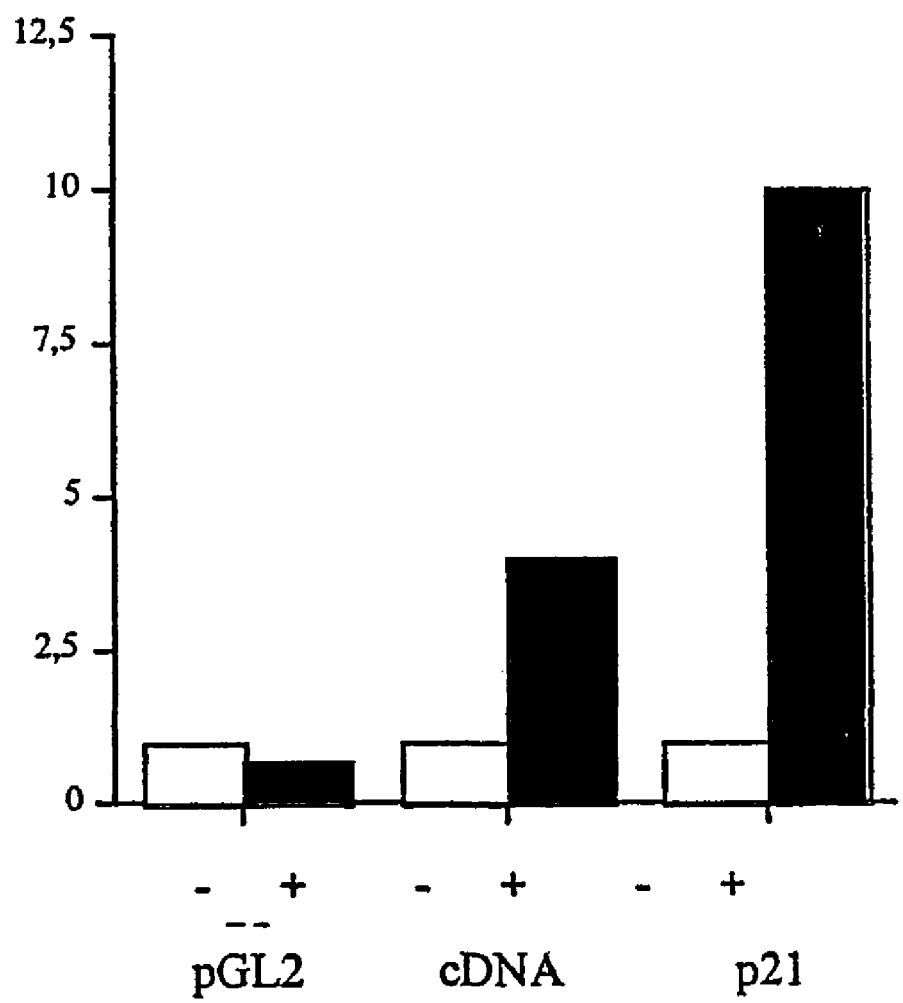
FIG. 9. Transcription-promoter activity of a 3761 bp fragment containing the first intron, the first exon and the region contiguous to the 5'-end of the first exon. The fragment was subcloned upstream of the luciferase gene and co-transfected with p53-expressing or p53-defective vectors. p21 promoter was used as control for the p53-responsive control gene. Sub-cloning vector: PGL2.
Figure 10:
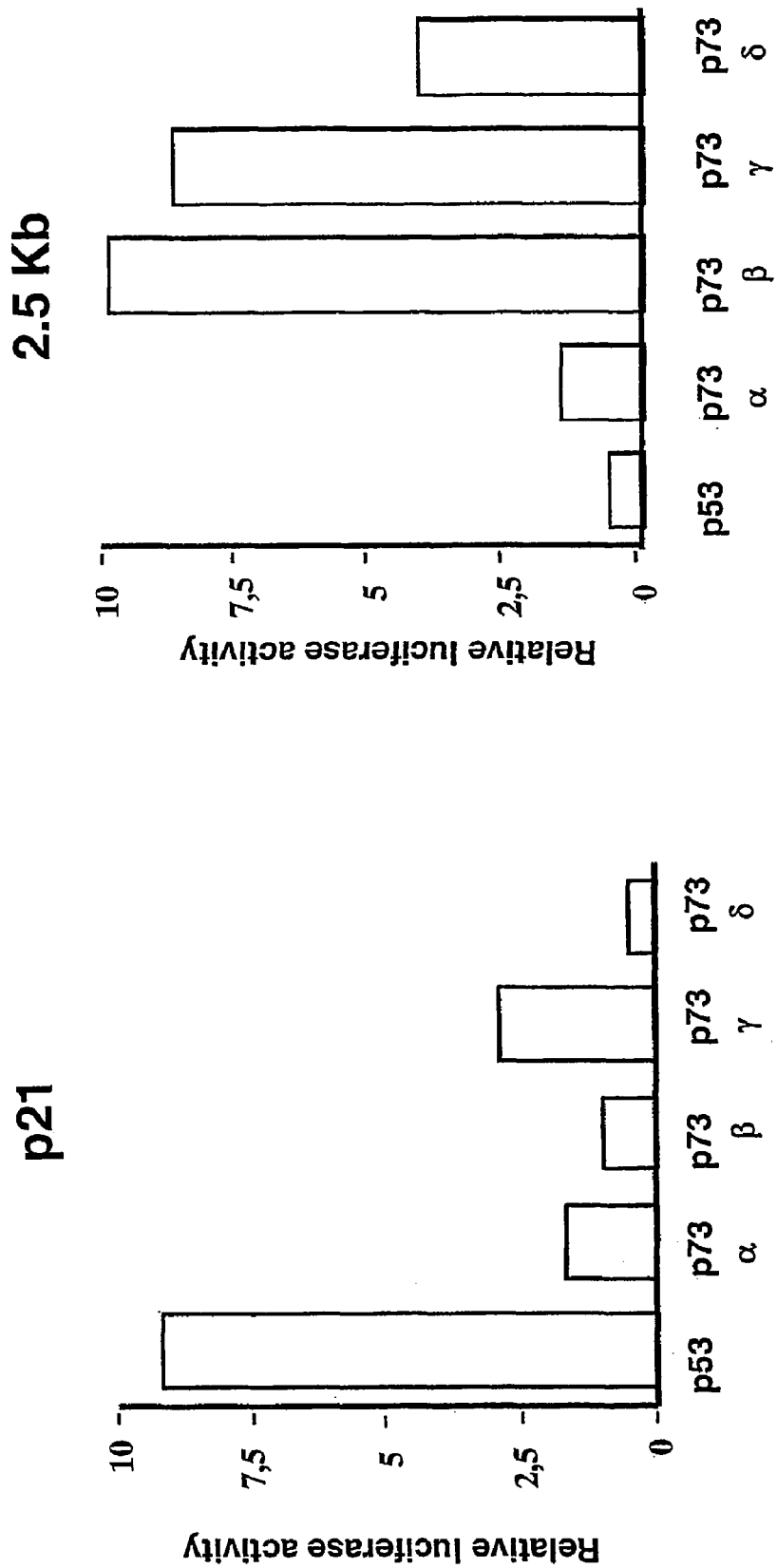
FIG. 10. Transcription-promoter activity of 2.5 Kb fragment linked to luciferase gene was evaluated in p53 (−/−) Saos-2 cells in cotransfection experiments with p73 different isoforms and p53. Activation of 2.5 Kb lo fragment was compared with p21 promoter.

In co-transfection experiments, the cells were transfected with both the same construct and an expression vector containing the entire p53 gene under the control of a strong viral promoter. In the presence of p53, the isolated fragment (3761 bp) induced a transcription of the reporter gene two fold higher than in its absence, which is consistent with the results of the experiments carried out in isogenic models differing for p53 expression (FIG. 9).

Example 8

Role of p73 in Gene Transcription

Different isoforms of p73 are generated by alternative splicing of p73 gene. The full length protein is defined as alpha p73 and at least 4 isoforms (beta, gamma, delta and epsilon) have been described so far. These isoforms can have different transcriptional activation potency. An additional, truncated form of p73 lacking the first 3 exons has been described. This form, named DNp73, does not result from a different splicing, but utilizes an additional promoter, positioned between exons 3 and 4 of the wt protein. The DNp73 protein has been shown to bind DNA but is not able to activate transcription for lack of the transactivation domain.

Experiments were carried out in which the 3761 bp fragment (SEQ ID n. 6) was subcloned in the pGL2 vector upstream of the luciferase gene and used to determine p73-dependent gene transcription. A further deletion of SEQ ID N. 6 generated a fragment of 2.5 Kb (SEQ ID N. 9) that was used to test the specific activity of different p73 isoforms.

Cells were co-transfected with the pGL2-derived construct and with expression plasmids containing the full-length regions coding for p53 and for different p73 isoforms. 48 hours after transfection, cells were lysed and the luciferase activity measured by standard, commercially available kits (Promega).

A typical experiment is reported in FIG. (10), showing the ability of p53 and of different p73 isoforms to activate the promoter region (single experiment).

p73 is a stronger activator of the promoter fragment than p53. Among different p73 isoforms, beta and gamma isoforms are the strongest.

Figure 11:
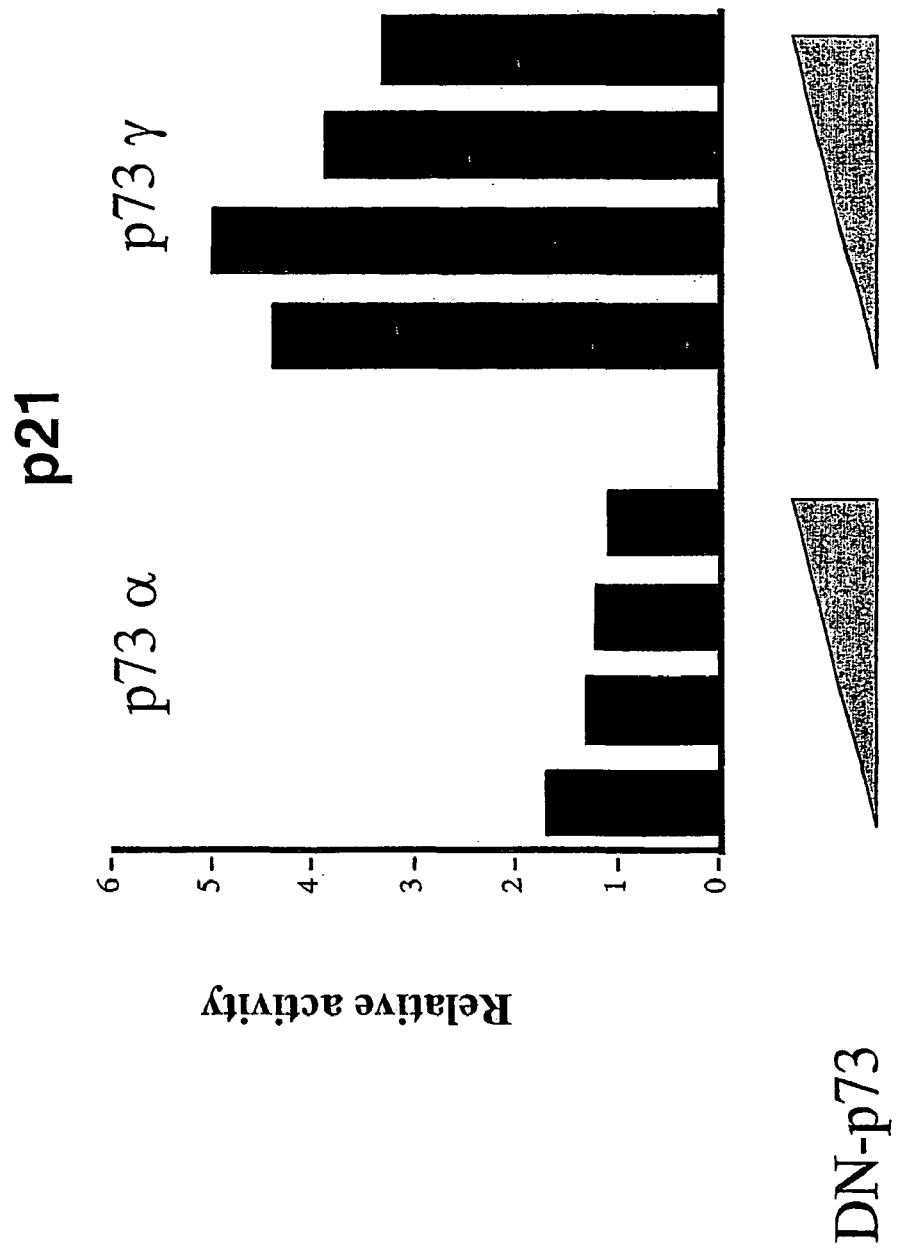
FIG. 11. DN-p73 repression of transcription activity of p73α and p73γ on p21-luciferase promoter. Increasing concentration of DN-p73 was used in co-transfection experiments with p73α and p73γ.
Figure 12:
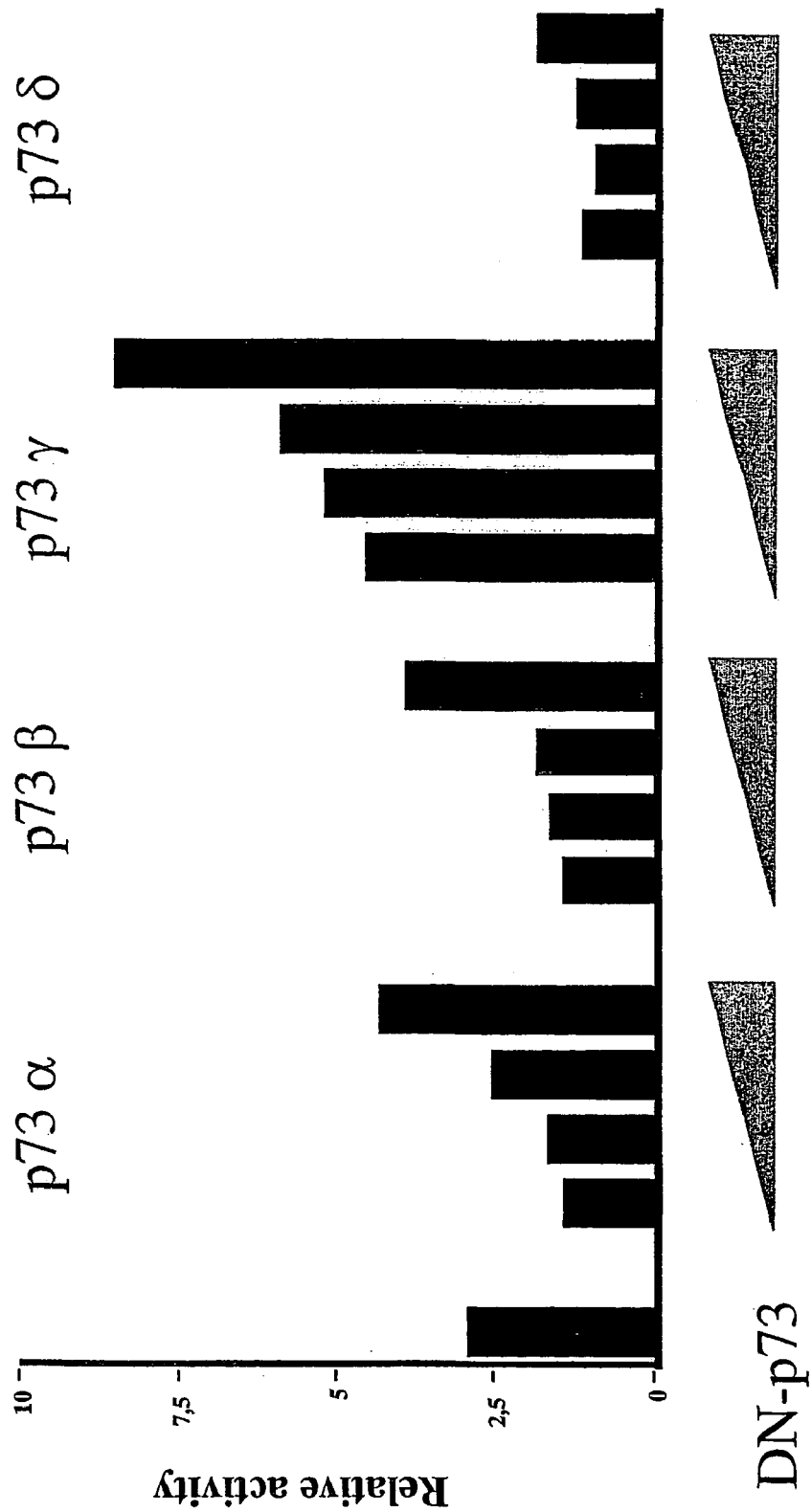
FIG. 12. DN-p73 cooperation with p73α, p73β, p73γ, p73δ in transactivation of 2.5 Kb fragment-luciferase construct with increasing concentrations of DN-p73. The first column shows induction of 2.5 Kb fragment by DN-p73 alone.

To test the ability of DN-p73 to block p73-induced transactivation, we have conducted experiments in which the promoter-luciferase construct has been cotransfected with the expression plasmid. As a control we have used the p21-luciferase construct. As expected, increasing the amount of DNp73, transactivation of p21 promoter by p73 tends to decrease (FIG. 11). With 2.5 Kb fragment-pGL2 construct, increasing amounts of DNp73 determined a concentration-dependent increase of luciferase activity, which suggests a cooperation between p73 and DNp73 in transactivating this DNA sequence. DNp73 is also able to transactivate 2.5 Kb fragment-luciferase construct when transfected in the absence of p53 or p73. This effect is not observed with the p21 promoter sequence (FIG. 12)

Example 9

Fragments Retaining Promoter Activity

Figure 13:
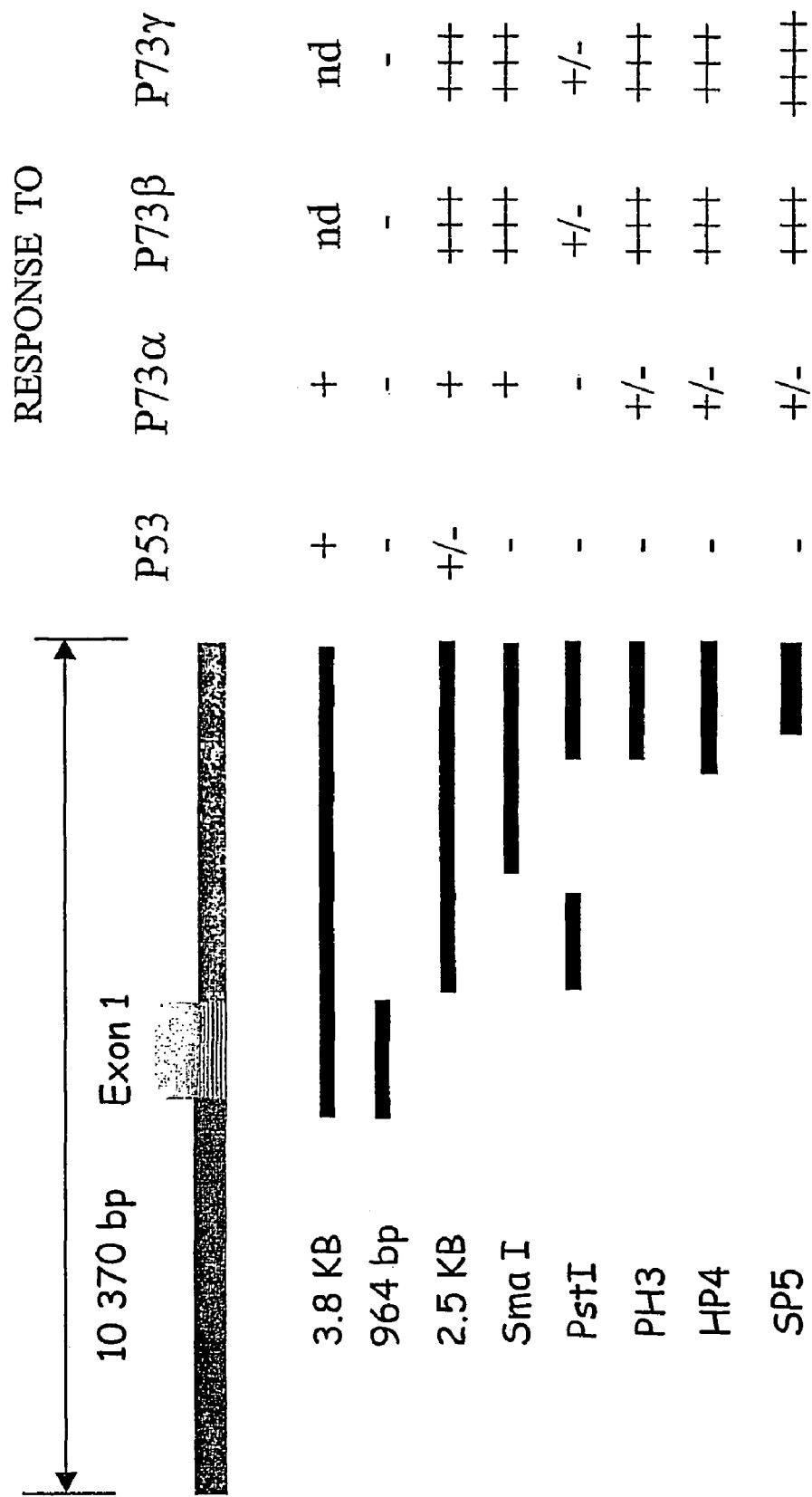
FIG. 13. Response of 3761 bp fragment and deleted mutants to p53 and p73α, p73β, p73γ, p73δ. Fragments were subcloned upstream to the luciferase gene. (the sequences of fragments 2.5 KB, SmaI, PstI(a)+PstI(b), PH3, HP4, SP5 and 964 bp are respectively reported in SEQ ID N.: 9, 10, 12+13, 11, 14, 15, 16)

Fragments of the 3761 bp DNA were generated (FIG. 13). These fragments, subcloned upstream to the luciferase gene, have been co-transfected with p73 and p53 expressing plasmids in an attempt to restrict the DNA region responsible for the p53- and p73-dependent transactivation.

In FIG. 13 the luciferase activities are reported. The sequence of 2.5Kb results particularly responsive to p73.

The fragment of 964 bp (SEQ ID N. 16) does not respond to any of the p73 isoforms nor to p53. Further deletions of the 3761 bp sequence retain a promoter activity responsive to p73, particularly to the beta and gamma isoforms, while the p53-dependent luciferase activity was almost abolished. The SP5 fragment (577 base pairs) is particularly responsive to p73 gamma.

Example 10

Isolation of Murine cDNA

In consideration of the high oncosuppressive effect exerted by the isolated gene, its murine homologue was cloned via PCR using primers derived from the human sequence. The identity was 87% for the nucleotide sequence and 88% for the amino acid sequence (SEQ ID N. 7-8, respectively).

The RNA from 3T3 murine fibroblasts was reverse-transcribed (random hexamers- RNA PCR kit Perkin Elmer) and used for the amplification of a 909bp fragment (primers 5'-ctcgagtgccatggcaggatagcacc [SEQ ID NO:17] and 5'-tcta-gatcatgcttctttcaacagtg [SEQ ID NO:18])

The isolated fragment (nt 1-906; the terminal "tga" is a stop codon) codes for a 302 aa polypeptide (i.e. 1 aa less than the corresponding human polypeptide).

The invention claimed is:

1. An isolated DNA molecule selected from the group consisting of SEQ ID NOS:5, 6, 9, 10, 11, 14, 15, and a construct comprising, from 5' to 3', SEQ ID NO:12 and SEQ ID NO:13, which when operably associated with a gene, regulates expression of that gene.

2. An isolated DNA molecule according to claim 1, having transcription promoter activity responsive to p53, and comprising SEQ ID NOS:5, 6, or 9.

3. An isolated DNA molecule according to claim 1, having transcription promoter activity responsive to p73, which is selected from the group consisting of SEQ ID NOS:5, 6, 9, 10, 11, 14, 15, and a construct comprising, from 5'to 3', SEQ ID NO:12 and SEQ ID NO:13.

4. A genetic construct, comprising a sequence selected from the group consisting of SEQ ID NOS: 5,6, 9, 10, 11, 14, 15, and a construct comprising, from 5' to 3', SEQ ID NO: 12 and SEQ ID NO: 13, wherein the sequence is operably linked to a reporter gene, and wherein the sequence regulates expression of said reporter gene.

* * * * *

UNITED STATES PATENT AND TRADEMARK OFFICE
CERTIFICATE OF CORRECTION

PATENT NO. : 7,189,840 B2 Page 1 of 1
APPLICATION NO. : 10/483241
DATED : March 13, 2007
INVENTOR(S) : Massimo Broggini It is certified that error appears in the above-identified patent and that said Letters Patent is hereby corrected as shown below:

Column 2, line 3, after "regulation of protein synthesis." delete paragraph break.

Column 3, line 31, "ability of the e compound" should read --ability of the compound--.

Column 4, line 19, "with the. distamycin-A" should read --with the distamycin-A--.

Column 5, line 7, after "cDNA library" delete paragraph break.

Column 5, line 8, delete "Human ovary carcinoma A2780 cells were treated for 1 hour with an".

Signed and Sealed this

Seventh Day of August, 2007

JON W. DUDAS
*Director of the United States Patent and Trademark Office*

SEQUENCE LISTING

<160> NUMBER OF SEQ ID NOS: 19

<210> SEQ ID NO 1
<211> LENGTH: 5338
<212> TYPE: DNA
<213> ORGANISM: Homo sapiens

<400> SEQUENCE: 1

```
ccgaagccgg cgaccgcccc acctcctccc tccctcccgc ccgcttcctc tgcccacagc      60
gccggccaga gcgagctaga caagggcacg cggggcctcg cctagacccg agaagactgc     120
gggcgcgcgc aagcggcggc gtggaagctg tgagcgcccc catcccggag gtctccgccg     180
gctcccgggt gaatcagctc ccggccgact ttaggattct tctggatttt aaattttttc     240
tttttaaaaa aacttggacg gataaaagat gtgccatggc aggatagcac caaagagcac     300
ctcagtgttt gccgtggcct ccgtgggaca tggagtgttc cttccgctag tgatcctttg     360
caccctgctt ggagacggac ttgcttccgt gtgcccccta ccaccggagc cagagaatgg     420
tggctacatc tgccacccc ggccctgcag agacccctg acagcaggca gtgtcatcga      480
atacctgtgt gctgaaggct acatgttgaa gggcgattac aaatacctga cgtgtaagaa     540
tggcgagtgg aaaccagcca tggagattag ctgccgtctc aacgaggata agacaccca     600 cacatcactt ggggtcccca cgctgtctat agtggcttct actgccagct ccgtggcgct     660
cattctcctc ctcgtggtgc tgtttgtgct gctgcagcca aagctgaagt cttccatca     720 tagcaggcgt gaccagggg tatctgggga ccaggtctcc atcatggtgg atggagtcca     780
ggttgcacta ccatcatacg aggaggctgt atatggcagt tctggtcact gtgtgccacc     840
tgctgacccc agagtacaga ttgtgctgtc agaagggtct gggcccagtg ggaggagcgt     900
gccaagggag caacagctgc cggaccaagg ggcctgctcc tctgcaggtg gagaagatga     960 ggccccagc cagtctggac tatgtgaagc ctggggctct cgggcctcag agactgtgat    1020
ggtgcatcag gcaaccacct cttcctgggt ggccggctca gggaaccgcc aactggcaca    1080
caaagaaact gcagattcag agaacagtga catacaaagc cttttatccc tcacgtcaga    1140
ggagtacaca gatgatattc cactgttgaa agaagcatga gggcagcggc cagcctttcc    1200
tctctgcgag gttctctcag cccttcctcc ctctccctgt gggattgagc accctgtact    1260
ctccagccac cttacctgga tacctgagct gccacctgtg tatctgtgta tctctgaggg    1320
ccctataggc ccaccttgct ggaaactcaa ggaagattct cgccatctgc ctgttggaca    1380
gctggaggag ctggctcttt gcctggcccc gccttcccat ctgtcagaga catatttgaa    1440
tgtgctggat caaaccctcc cttttcctaa gcctctgggt cccctccagc cagctctttg    1500
gcggcagccc ccaccagctc ctgtgggcct gagtgctgct gtgtttactt gtgcctttcc    1560
cccaccctgt ccagtttccc tgtcatgcag acttgttgct gtccacaagc cttagtggct    1620
gcactgctgc ccctgccac acagggggcc gggcctgggt ctgtcctgtt tcctttgagg    1680
gttgccccta ctgccctttg caggaacaga tccaggtgtg agagctcttg agtcaagagt    1740
```

```
ggcagaagtg gctctaattg gggtgagagt gtagtccctg ggcttgccct gggttgaccc    1800
tggtggcata tttccttggc cgaggatgga agatttggag aatcatgtcc atgctggccc    1860
aggacccagc catctggccc aaaggcacaa gctcctggcc ctgttgagtt gagagtttcc    1920
aagaagcatc cagaagatcc caagggagag aaggaaaatg gctgataatg attgtcttcc    1980
taatatgcaa gttctcactt cctacttcca gcatcggcct tcctggcctt gtcttttttt    2040
tgtttccctg gagtataatg ggaagttgca tgctgcctcc tgggttttat cccagatagc    2100
tctggctttc ttgctgccca caggggcctg gggcaggaag gagacttgct gagatgccat    2160
ggagtgccca tctggtcact ggcagtctgg gcaggttgcc cctttctggg tttgtggtga    2220
cggaggggag gccgagaggc acagaccaag tccccgggtg gctgcaggca gctccagccc    2280
ggtcctgagg atcctcctca ccatggtcac gtgccttagt aactgtgccc aggaagtggc    2340
ctgctgcttg ctgtgctgct gcttttccta cttctgccct tccctgccac ccctcgcatg    2400
tcacagctga caagcaattc cttgtcttcc ctggccccct gggggaaggg ctgagaaaca    2460
gtccatgtgc accccaacct taatggcctg aggtgggcag aggggtgtgg agcagcctgg    2520
agtacagggc cctgggggag gagcccactg atgaggggcg ctctcccata gccatgtgtt    2580
gaatgctaac taggctgggg tggacgaact ctgccaactg ctgtcatctt agaagataga    2640
tgcagcagta aggaatgttt gttttgcttt tttctgaaat tttctgaagc actgtggctg    2700
ggaaacttcg aagcggaccc tgtgctgcat gtctgctcct cccctgagcc tgtctgcttg    2760
ggggtggtaa aaataaaaat cccagtttat tttcagtacc ttacctaaca gggttggctc    2820
caggcgtggg tggcctagaa gatgagggga gtggtcttct cccagccttt taccctcttg    2880
cctcctgcct ccgcgcttac acacgcactt taccacccgg tcattccctg gcctcttgct    2940
gccacttgta gtcttccttc cttcctctca gggtaagggc agtgcctgct gtgcctgttg    3000
gccactccca cacttcccct cccccaggag ccctcatctg ctgtgctgag tccaggaaag    3060
catagttagg tagggagctg gttggagaag gtgctagaac tagaaggcag atgagactag    3120
catgggccca cctggagggc tgtccctaat ggccccagtc gccttacctc acccacagca    3180
gtgcccttgt cttcctccaa aacagaaagc agtgacaaaa gggggagggg tggtaatctg    3240
aagtctcact gctgagcctt cagcttttat ttttcactgt ttcaaaaccc gcattctatt    3300
ctagaatggt ttttaaaatg gaagatctta ccttttttcta tcttgttact ctggggtttt    3360 gtcccccctaa gagattgcac tttttgtttg gggtttattc agctgcatag atgaccagct    3420
tgatccctgg tgaaatgaaa agccttcctt ctcctgaagc ctctttccgc cctgccctcc    3480
actaacaaca ctgaggagca caagcccagg cttgccacc tggtaggaaa ggaagaaatt    3540
agaacaatgg gagccttggc tcccctctcg tctcctcccc tccttcttgt cactggcttt    3600
gatgaggccc acttcccaga ggctcctggg cctgtgagtg caggagctca ttctcccctc    3660
actgctgaag tctgtgacag cttcttcctc cagttatgtc tttcttccaa agcaatttct    3720
taaccatcag ccatgtgctg ctatttctag ggcttctggg cttttgtccct tactgagaga    3780 ttagggactc cacagctgcc ttgaggtagg gcctggctga gagacaaggg tagcagcagg    3840
tggcaggctg ttaaaagaca ggctgcctga ggagcctgga gcaggtggaa acaggtggaa    3900
gaaaccggcc acagccctgc tttaccgggc tcacctctag ggcattccag caagaggctg    3960
atgcaggaga atggccagca ccaaaggaca tttaaaagag ttttttgggtt ttttttgtttg    4020 tttgttgttg gtgtttgttt tttttttttt tttttttggca cacttgagct gactcagtgc    4080
aggtttaata tcctggtgac ttgcagtcac attctaatga ctttcaaggg ccagaatatg    4140
```

```
gtgaaaatca cttaaaatat ccgtcccttc catgccttag tttagcaggt aggctctatc    4200
ttttgccatt tctgtatttt atgtgctgtg ttcccgtttc actgggtatg aactgtgaaa    4260
tggactgaat cctggccact ttatgagttt gtttggtttt ataaggcatt tcaatgtaca    4320
ttctataaat acaagcactc catttgcaaa cagatcttaa gctaatattt tctttcccat    4380
tcatcttgcc ctcccctcc tcccaccagc tttaaagttc agtggagaag ccagatggca     4440
attcagacaa aggtatactc ttcctgcttc atgggtggtg gcacgggaat agatagccct    4500
tagccctttc cctcccagtc ccagctgagc cctcagacca cttgcttccc acataacaat    4560
gtcgcctcca tttccgagga acatccttgc gtagagaatg aaatatgctg caatcatttc    4620
tgcatcctta ctcctcaccc ccaaagaaaa aaaaaggcc tagcagggaa gcagcatgca     4680
ggcttcacag cttaatgcca aggacagcga gtgaggctgg gagcttctct tgggcctgct    4740
gggtctgtca gctctcggaa tagggacagt ccttactggt gccccaaggt gggacttgga    4800
gaatattttg cttggcatat gtttggtctg aatggtgtag ttgctggttc cctagagagg    4860
aaaaggtggc aggcccagct ttgctgggaa atggctctta atttccagtt gaaaccctag    4920
tagaattgtg aatgaaaacc tcaaggttga gcccctctgc caagcagcag agctagtaga    4980
aggggatgca gggcaaagc actcagttgc caagcaagga ggagagatgt acgtgggctg     5040
tgtggcagtc cccacaccct gccctggctt cttcaggtta tcgcaccact atggaatcct    5100
ttgcagaatg gtactcatat aatggtttaa acaacacat tcataattga ctctgtgcag     5160
gatgtcactc aatcagtttg ggtttgcttt attttatttt atatatatat tttttggtat    5220
cctgtacatt gcagtgggtg tgaagatagt attttaatat ttgtacaaag tttaatttaa    5280
ttttaattgt tctatgtata taactgcatt tctaataat taaaaaaaag ttcttatg       5338
```

<210> SEQ ID NO 2
<211> LENGTH: 303
<212> TYPE: PRT
<213> ORGANISM: Homo sapiens

<400> SEQUENCE: 2

```
Met Cys His Gly Arg Ile Ala Pro Lys Ser Thr Ser Val Phe Ala Val
1               5                   10                  15

Ala Ser Val Gly His Gly Val Phe Leu Pro Leu Val Ile Leu Cys Thr
            20                  25                  30

Leu Leu Gly Asp Gly Leu Ala Ser Val Cys Pro Leu Pro Pro Glu Pro
        35                  40                  45

Glu Asn Gly Gly Tyr Ile Cys His Pro Arg Pro Cys Arg Asp Pro Leu
    50                  55                  60

Thr Ala Gly Ser Val Ile Glu Tyr Leu Cys Ala Glu Gly Tyr Met Leu
65                  70                  75                  80

Lys Gly Asp Tyr Lys Tyr Leu Thr Cys Lys Asn Gly Glu Trp Lys Pro
                85                  90                  95

Ala Met Glu Ile Ser Cys Arg Leu Asn Glu Asp Lys Asp Thr His Thr
            100                 105                 110

Ser Leu Gly Val Pro Thr Leu Ser Ile Val Ala Ser Thr Ala Ser Ser
        115                 120                 125

Val Ala Leu Ile Leu Leu Val Val Leu Phe Val Leu Leu Gln Pro
    130                 135                 140

Lys Leu Lys Ser Phe His His Ser Arg Arg Asp Gln Gly Val Ser Gly
145                 150                 155                 160
```

```
Asp Gln Val Ser Ile Met Val Asp Gly Val Gln Val Ala Leu Pro Ser
                165                 170                 175

Tyr Glu Glu Ala Val Tyr Gly Ser Ser Gly His Cys Val Pro Pro Ala
            180                 185                 190

Asp Pro Arg Val Gln Ile Val Leu Ser Glu Gly Ser Gly Pro Ser Gly
        195                 200                 205

Arg Ser Val Pro Arg Glu Gln Gln Leu Pro Asp Gln Gly Ala Cys Ser
210                 215                 220

Ser Ala Gly Gly Glu Asp Glu Ala Pro Gly Gln Ser Gly Leu Cys Glu
225                 230                 235                 240

Ala Trp Gly Ser Arg Ala Ser Glu Thr Val Met Val His Gln Ala Thr
                245                 250                 255

Thr Ser Ser Trp Val Ala Gly Ser Gly Asn Arg Gln Leu Ala His Lys
                260                 265                 270

Glu Thr Ala Asp Ser Glu Asn Ser Asp Ile Gln Ser Leu Leu Ser Leu
        275                 280                 285

Thr Ser Glu Glu Tyr Thr Asp Asp Ile Pro Leu Leu Lys Glu Ala
    290                 295                 300
```

<210> SEQ ID NO 3
<211> LENGTH: 4158
<212> TYPE: DNA
<213> ORGANISM: Homo sapiens

<400> SEQUENCE: 3

```
gggcagcggc cagcctttcc tctctgcgag gttctctcag cccttcctcc ctctccctgt      60
gggattgagc accctgtact ctccagccac cttacctgga tacctgagct gccacctgtg     120
tatctgtgta tctctgaggg ccctataggc ccaccttgct ggaaactcaa ggaagattct     180
cgccatctgc ctgttggaca gctggaggag ctggctcttt gcctggcccc gccttcccat     240
ctgtcagaga catatttgaa tgtgctggat caaaccctcc cttttcctaa gcctctgggt     300
cccctccagc cagctctttg gcggcagccc ccaccagctc ctgtgggcct gagtgctgct     360
gtgtttactt gtgcctttcc cccacccctgt ccagttttcccc tgtcatgcag acttgttgct     420
gtccacaagc cttagtggct gcactgctgc ccctgccac acaggggcc gggcctggt      480 ctgtcctgtt tcctttgagg gttgccccta ctgcccttttg caggaacaga tccaggtgtg     540
agagctcttg agtcaagagt ggcagaagtg gctctaattg gggtgagagt gtagtccctg     600
ggcttgccct gggttgaccc tggtggcata tttccttggc cgaggatgga agatttggag     660
aatcatgtcc atgctggccc aggacccagc catctggccc aaaggcacaa gctcctggcc     720
ctgttgagtt gagagtttcc aagaagcatc cagaagatcc caagggagag aaggaaaatg     780
gctgataatg attgtcttcc taatatgcaa gttctcactt cctacttcca gcatcggcct     840
tcctggcctt gtcttttttt tgtttccctg gagtataatg ggaagttgca tgctgcctcc     900
tgggttttat cccagatagc tctggctttc ttgctgccca caggggcctg gggcaggaag     960
gagacttgct gagatgccat ggagtgccca tctggtcact gcagtctggg caggttgcc    1020 cctttctggg tttgtggtga cggaggggag gccgagaggc acagaccaag tccccgggtg    1080
gctgcaggca gctccagccc ggtcctgagg atcctcctca ccatggtcac gtgccttagt    1140
aactgtgccc aggaagtggc ctgctgcttg ctgtgctgct gcttttccta cttctgccct    1200
tccctgccac ccctcgcatg tcacagctga caagcaattc cttgtcttcc ctggcccct    1260 gggggaaggg ctgagaaaca gtccatgtgc accccaacct taatggcctg aggtgggcag    1320
```

```
agggtgtgg   agcagcctgg   agtacagggc   cctgggggag   gagcccactg   atgaggggcg   1380
ctctcccata  gccatgtgtt   gaatgctaac   taggctgggg   tggacgaact   ctgccaactg   1440
ctgtcatctt  agaagataga   tgcagcagta   aggaatgttt   gttttgcttt   tttctgaaat   1500
tttctgaagc  actgtggctg   ggaaacttcg   aagcggaccc   tgtgctgcat   gtctgctcct   1560
cccctgagcc  tgtctgcttg   ggggtggtaa   aaataaaaat   cccagtttat   tttcagtacc   1620
ttacctaaca  ggggttggctc  caggcgtggg   tggcctagaa   gatgagggga   gtggtcttct   1680
cccagccttt  taccctcttg   cctcctgcct   ccgcgcttac   acacgcactt   taccacccgg   1740
tcattccctg  gcctcttgct   gccacttgta   gtcttcctttc  cttcctctca   gggtaagggc   1800
agtgcctgct  gtgcctgttg   gccactccca   cacttcccct   ccccaggag    ccctcatctg   1860
ctgtgctgag  tccaggaaag   catagttagg   tagggagctg   gttggagaag   gtgctagaac   1920
tagaaggcag  atgagactag   catgggccca   cctggagggc   tgtccctaat   ggccccagtc   1980
gccttacctc  acccacagca   gtgcccttgt   cttcctccaa   aacagaaagc   agtgacaaaa   2040
ggggagggg   tggtaatctg   aagtctcact   gctgagcctt   cagcttttat   ttttcactgt   2100
ttcaaaaccc  gcattctatt   ctagaatggt   ttttaaaatg   gaagatctta   ccttttttcta 2160
tcttgttact  ctggggtttt   gtcccccctaa  gagattgcac   ttttttgtttg  gggtttattc   2220
agctgcatag  atgaccagct   tgatccctgg   tgaaatgaaa   agccttcctt   ctcctgaagc   2280
ctctttccgc  cctgccctcc   actaacaaca   ctgaggagca   caagcccagg   cttgcccacc   2340
tggtaggaaa  ggaagaaatt   agaacaatgg   gagccttggc   tccctctcg    tctcctcccc   2400
tccttcttgt  cactggcttt   gatgaggccc   acttcccaga   ggctcctggg   cctgtgagtg   2460
caggagctca  ttctccccctc  actgctgaag   tctgtgacag   cttcttcctc   cagttatgtc   2520
tttcttccaa  agcaatttct   taaccatcag   ccatgtgctg   ctatttctag   ggcttctggg   2580
cttgtccct   tactgagaga   ttagggactc   cacagctgcc   ttgaggtagg   gcctggctga   2640
gagacaaggg  tagcagcagg   tggcaggctg   ttaaaagaca   ggctgcctga   ggagcctgga   2700
gcaggtggaa  acaggtggaa   gaaaccggcc   acagccctgc   tttaccgggc   tcacctctag   2760
ggcattccag  caagaggctg   atgcaggaga   atggccagca   ccaaaggaca   tttaaaagag   2820
ttttttgggtt ttttttgtttg  tttgttgttg   gtgtttgttt   tttttttttt   tttttttggca 2880
cacttgagct  gactcagtgc   aggtttaata   tcctggtgac   ttgcagtcac   attctaatga   2940
ctttcaaggg  ccagaatatg   gtgaaaatca   cttaaaatat   ccgtcccttc   catgccttag   3000
tttagcaggt  aggctctatc   ttttgccatt   tctgtatttt   atgtgctgtg   ttcccgtttc   3060
actgggtatg  aactgtgaaa   tggactgaat   cctggccact   ttatgagttt   gtttggtttt   3120
ataaggcatt  tcaatgtaca   ttctataaat   acaagcactc   catttgcaaa   cagatcttaa   3180
gctaatattt  tcttttcccat  tcatcttgcc   ctcccctcc    tcccaccagc   tttaaagttc   3240
agtgagaag   ccagatggca   attcagacaa   aggtatactc   ttcctgcttc   atgggtggtg   3300
gcacgggaat  agatagccct   tagccctttc   cctcccagtc   ccagctgagc   cctcagacca   3360
cttgcttccc  acataacaat   gtcgcctcca   tttccgagga   acatccttgc   gtagagaatg   3420
aaatatgctg  caatcatttc   tgcatcctta   ctcctcaccc   ccaaagaaaa   aaaaaggcc   3480
tagcagggaa  gcagcatgca   ggcttcacag   cttaatgcca   aggacagcga   gtgaggctgg   3540
gagcttctct  tgggcctgct   gggtctgtca   gctctcggaa   tagggacagt   ccttactggt   3600
gccccaaggt  gggacttgga   gaatattttg   cttggcatat   gtttggtctg   aatggtgtag   3660
ttgctggttc  cctagagagg   aaaaggtggc   aggcccagct   ttgctgggaa   atggctctta   3720
```

| | |
|---|---|
| atttccagtt gaaaccctag tagaattgtg aatgaaaacc tcaaggttga gcccctctgc | 3780 |
| caagcagcag agctagtaga aggggatgca ggggcaaagc actcagttgc caagcaagga | 3840 |
| ggagagatgt acgtgggctg tgtggcagtc cccacaccct gccctggctt cttcaggtta | 3900 |
| tcgcaccact atggaatcct ttgcagaatg gtactcatat aatggtttaa acaacacat | 3960 |
| tcataattga ctctgtgcag gatgtcactc aatcagtttg ggtttgcttt attttatttt | 4020 |
| atatatatat ttttggtat cctgtacatt gcagtgggtg tgaagatagt attttaatat | 4080 |
| ttgtacaaag tttaatttaa ttttaattgt tctatgtata aactgcatt tctaaataat | 4140 |
| taaaaaaaag ttcttatg | 4158 |

<210> SEQ ID NO 4
<211> LENGTH: 912
<212> TYPE: DNA
<213> ORGANISM: Homo sapiens

<400> SEQUENCE: 4

| | |
|---|---|
| atgtgccatg gcaggatagc accaaagagc acctcagtgt ttgccgtggc ctccgtggga | 60 |
| catggagtgt tccttccgct agtgatcctt tgcaccctgc ttggagacgg acttgcttcc | 120 |
| gtgtgccccc taccaccgga gccagagaat ggtggctaca tctgccaccc ccggccctgc | 180 |
| agagaccccc tgacagcagg cagtgtcatc gaatacctgt gtgctgaagg ctacatgttg | 240 |
| aagggcgatt acaaatacct gacgtgtaag aatggcgagt ggaaccagc catggagatt | 300 |
| agctgccgtc tcaacgagga taaagacacc cacacatcac ttggggtccc cacgctgtct | 360 |
| atagtggctt ctactgccag ctccgtggcg ctcattctcc tcctcgtggt gctgtttgtg | 420 |
| ctgctgcagc aaagctgaa gtcttccat catagcaggc gtgaccaggg ggtatctggg | 480 |
| gaccaggtct ccatcatggt ggatggagtc caggttgcac taccatcata cgaggaggct | 540 |
| gtatatggca gttctggtca ctgtgtgcca cctgctgacc ccagagtaca gattgtgctg | 600 |
| tcagaagggt ctgggcccag tgggaggagc gtgccaaggg agcaacagct gccggaccaa | 660 |
| ggggcctgct cctctgcagg tggagaagat gaggccccag gccagtctgg actatgtgaa | 720 |
| gcctggggct ctcgggcctc agagactgtg atggtgcatc aggcaaccac ctcttcctgg | 780 |
| gtggccggtc agggaaccg ccaactggca cacaaagaaa ctgcagattc agagaacagt | 840 |
| gacatacaaa gcctttatc cctcacgtca gaggagtaca cagatgatat tccactgttg | 900 |
| aaagaagcat ga | 912 |

<210> SEQ ID NO 5
<211> LENGTH: 10735
<212> TYPE: DNA
<213> ORGANISM: Homo sapiens

<400> SEQUENCE: 5

| | |
|---|---|
| ctttcagttt tccagatgta aattttcaca tttcaattgt aaatgtttag caacttgttc | 60 |
| tataggtggg agctgattta tatttagtaa tttctgtggt gtaaatactt ccactgtatc | 120 |
| tgatttcaaa ctatcaatgt gatgtcactg aatgtggagt tgagaagaga tgagaagtgg | 180 |
| cataatatga tgtagtactt cataagagat gtaaataaac ttgaaagcat agataagagt | 240 |
| ataatgtaag agaagggagg cagaaaaagt aaaaaaatac aatgtagtaa aataattaat | 300 |
| aattaggaag tggtaacttg agtatttatt actttaacaa ctataattta attttacata | 360 |
| tatataattt aatttttta attttaatt ttttggttt ttttgagac agagtcttgc | 420 |

-continued

| | |
|---|---|
| tctgtcacct aagctggagt gtagtggcac aatcacagct tactttagtc ctgacctccc | 480 |
| gagctcaaat aatcctccca cctcagcctc ctgagtagct gggaccacag gcgtgtgcca | 540 |
| ccatgcctgg ctaattttg tattttttgt aaagaggtct cactctgttg cccaggctgg | 600 |
| tctcaaactt ctgagctcaa gtgatcctcc tgctttggcc tcccaaagtg ctgggattac | 660 |
| aggcgtgagc cactgctact ggccataatt taattttaa caaggctgt gtttaacaac | 720 |
| tagcttacaa aaatcttgaa catttagaa ttgattcttg acagtttgag cactcttcag | 780 |
| cacaccactg caggtaacct gctctggtcc ccctttaaaa atcacatttg gtttttacag | 840 |
| tgcaaattac agctgtattc cctaagaagc aggacatgct actagtaact gtggccttgg | 900 |
| cctcatcttt aaactttatg tacctcagtt tcctcatatg caaaatgaag ataatagtat | 960 |
| taatacctat ttcagaggct attgcaagga ttaaataaaa tcatgtatgt ggagccacta | 1020 |
| gcaaagtatc tggcagacag tacatattta atgtattgga gcttttttca ggggattcat | 1080 |
| tgacatgcct gggggcaaag ctgcaccttg ggtccatca tcagcacctt caaaataccc | 1140 |
| tgattttgga ggtatcaaaa taccctgatt ttgaaggtcc ctggccagcc aaaagaggga | 1200 |
| ctgaccctac tgatccagcc aacaagtcct ggagccaaga accttctgag gtgttgtgtc | 1260 |
| tgccagagct tcacagccct atccctgcct ccccagacag tctgaaggag ggagcaactc | 1320 |
| cattcctcta tgcactggca gctcagagct agcaaggcca atcatatagc tctgtcttct | 1380 |
| caccattaaa tcacatgaaa atgaaccatc agggagggaa tacagtgtcc aatgaccagg | 1440 |
| agctgtgtgt gtgtgtaggt gtgtgtgtgt gtatatgtgt gtgtgtgtgt gtgtgtgtgt | 1500 |
| gtatgtggga ggggtttgtg ggctggctct gtctagaaag gcctcaggcc ctaggctatc | 1560 |
| cccagtccct tccttcctcc ctgcagattg tctcctagag tcactgccca gcccttgggc | 1620 |
| aaagggcaag cagcaggtca tcaggctggt tggcaccagg ggtgggggg atctgatatt | 1680 |
| cattcatctt ccactgggat accatctgga gacatagcag gtggatgctc cctttctacc | 1740 |
| ttggcttttc cttgtgtgaa aaatggggcc aacacttta ccagttaacc tgacctgtat | 1800 |
| tagggaaaga atgttgtcaa agacatgctt cagaaaagca ggtggggctg ggttgccctc | 1860 |
| ttatatgtat ctgctaattg ggcagcctca agtgcacatt ttctaaggct agggtcagag | 1920 |
| ttggggtgga tagggaatca tagctgctgc tgtgaatagc ccagatctaa gccctgaact | 1980 |
| ctgacctcta caaagctccc tccgaccagt ggcctgcagg gattgcgtca ccaagcctgg | 2040 |
| ctctcacagg ctcctgacaa gctgcaagaa gggttgcccc tggtgatggt gcaggctcac | 2100 |
| aaattcagat aacctcctga gcctagatct tcctcctctg gagtgggagt tgcttctcag | 2160 |
| ctcctgttgg cctagccctg tacagcccac ccattttgga ctctgacatt ctgcggtgag | 2220 |
| ggtggcctca ccttccacct cctctggggt caaatgggtt taccttcaca gggctttgaa | 2280 |
| agctgcccaa ggaatcttga atcaaaacat gaaactcatg ctaatttcta tatgagatca | 2340 |
| gacaagctag caacctttca gtgcctcaac ttccttatag gtaaaattgg ggacaataat | 2400 |
| gtctcttcgt tttatgggga tgttgtaaaa aactagctgg tatgcaaaaa agcactttt | 2460 |
| taaaaagcaa gagatatatg aggacaattt caatctttat ttgctatttt tattagggt | 2520 |
| gggaggaagc acatggttta tttgggaaag tgtgaccttt ggaacagaca aacaagaatg | 2580 |
| aattctgctt ttgcaacata catacttatg tggttttgat atgtcaaaaa aaaaaatctc | 2640 |
| tctaagcctt gcttgtaaaa tggtgttaat gataattaac ttggaggact gttgccaaaa | 2700 |
| ttagaggtta cacgtatcaa gtccctacca agcacctgac atacagtagg tgctttgtaa | 2760 |
| atagtagctg tcattactac tattgtatgt aataaccata gcaactgaga ttccatgtac | 2820 |

```
ttattctgaa ccttttctct cactttcaga gagccaaact cctctgtcct gccctgcaag    2880
cagtaaaggc acacactcct tgttatattc ctgggagatg aaaggaatac tgtgcctcct    2940
gactcttatc ataggagtga ctacctcatc ctgattggcc caggactgtc ctaattttgg    3000
cactggaagt cccatgtgcc aggaatcccc ttagtcccag gcaaactggg atggctggct    3060
attctactca ccaccaactg gactaatct aaccccatg ccatattcca gcacctagat    3120
ttagagcaga atattaagat tgtgctgga aattggccag gtgtggtgac tcacgcctgt    3180
aatcctagca ctttgggagg cagaagcagg ctgatcactg aggtcaggag tttgagacca    3240
gcctggctaa cgtggtgaaa ccctgtctct actaaaaata caaaaattag ctgggtgtgg    3300
gggtacgcac ctatagtccc agctactcgg gagactgaga caggagaatc ccctgaacct    3360
gggaggcgga ggttgcagtg agctcagatc atgccactgc actccagcct gggcgacaga    3420
gcaagactcc gtcaaaaaaa aaaaaaaaa aaagatttat gctggaaatc tggaaggacc    3480
caggaatatt agctcaaaga gccatcttaa gtccttttag aataaggcag gtctgaatt    3540 gaaaagtgaa aataaaaaat tagctctggt ttaaaattga ttgttaggtg gaagaaacaa    3600
aaaatcaatt ataaaggcca catatttgta tgattctatt tatagagagt gctcagaata    3660
ggcaaatcta tagagacaga aagtagattg ttggttgcct agggagggag gcagggaagg    3720
tggtagggag ggaggaaatg gtagtgactg ctgatgggta tgggagttt ttttagggtc    3780 atgaaaatgt tctaaaatat tgtacgactc tgtaaatata ctaaaaacca ttgaattgtt    3840
cactctaaat gtacaattgt acatgtgcaa atttgtacaa tttgtaaagt tatacaaaat    3900
aaatacaaat ttaaactgtg aattgctggt atgtgaatat ctcaataaag ctgttaatta    3960
attaattaat ttatttaaga cacagtctca ctctgtcgcc caggctggag tgcagtggcg    4020
caatctcagc tcattgcagc ctctgcctcc caggttcaag caattcttgt gactagcctc    4080
ccacatagct gggattacag gcgtgcacca ccacgccagg ctaattttta tattttagt    4140 agagacgagg ttttgccatg ttggccaggc tggtcttgaa cttctggcct caaatgatca    4200
gcctgcctca gcttcccaaa atgctgggt tacaggtgtg agaaagctgt taaattaaaa    4260 aaaatctta aaattttaa agaattttat ttaaaaaat ctatgatccc tcccacttga    4320
gaatgtctaa gtctaaatta ttcttaacct tcatcttgtg agatctttc aatggcagaa    4380 agataatatt caccccaggc caggaagtac cattccattt tgcgggtgag aagagcaagg    4440
cctatacgta gaatgtaaca ggggcttttc gtcagctgta ctgaagaggc cagtggaact    4500 tcagataga ggggatgaga agacaggaaa ggctggtgag ctgacattta taagggagg    4560 agacttgacc ctgattctgg caattcaaag cagaaggaaa tggaagctaa tcccagctgt    4620
aacccagcta ctcgggagac tgaggcagga gaatccctg aacccgggag gcggaggttg    4680
cagtgagctc agatcatgcc actgcactcc agcctgggcg acagagcaag actccgtcaa    4740
aataaataaa taaataatta aatatttaaa atgtttaaaa attttaattt aatacttttc    4800
tgtggcactt tggggctcaa ccaaagtgcc acagaaaagt agaagcagca gccttgggaa    4860
gattctgaag ggtaagtaga aaggccttc aagattgagg aaacagcatg ggcacctggt    4920
ttgtgacagg aatggcttgt tagagaccag caggtggtat ggggaggctg gagtggggtg    4980
tgtggaggga tggagagcat ttgggccgga ctgtggacag cacaggatac tacagtcctt    5040
gctgatgact ttgagttcat tctgtggacc ctgaaggtct gggagaggat tttttttttt    5100
tgagacagtc tcactctgtc acccaggctg gaatgcaatg gcacgatctc ggctcactgc    5160
```

```
aacctctgct tcctgagttc aagcaattct cctgcctcag gctcctgaat agctaggatt    5220
acaggcatgt gccaccacgc ctggctaatt tttgtatttt tagtagagaa ggggtttcgc    5280
catgttgtcc aggctggtct caaactcctg acttcgtgat ctgcctgcct tagcctccca    5340
aagtgctggg attacaggcg tgagctaccg cgcccgactg aggattttg ggtagtgatg     5400 gacagatctg cataggtct cacaagggat tttataaggt ggcagttctt gtatgaagtt     5460
actgagcctc ttaatggcca aactgacttc agtgcacagc caggggctca gttactttgg    5520
cagttgatct gacctgaacc atccatgcct gctttcttcc cttcctttc tttcttttc     5580 tccttcctcc attcatcttc tccaattctt cctccatccc tttcccttgc ttccttcccc    5640
cttgtcccct ccctgagcct tgggtctgcc tggcatgttc ctgctgccca cactgatttg    5700
gttgtgctct gaggcagacc caggtagttc tgaattgtgc ttttcaatct tctagtggtc    5760
tgggcagtgt ggccccaaat gagcaggaag ggaggggtgc ccatcttctc taatgagtct    5820
ggacccaaga aggcaaggaa gaaagaaggc agaacaagga tagacttatg aaaaaggcat    5880
tatagcaacg agccacaggt tgctgtgggg cccagaaggg aagggttctt ttggggatgg    5940
gtctgtgtgc atgggagga gcatcctgtt tatttggttc aagctacttc acaaggacat     6000
gccctgttaa ttcacagtgc ttttcccgaa agcctactag aactaggcct ggtgagaggc    6060
cctgagaagg tgtatccttt tgtccaagag catctgggag aagaggcctg cctgacccaa    6120
gctgcagcaa agacacaagt ctgtaggtcc agatgtggac tctaccactg atttacaagt    6180
aggagttcct taacacttat ggaggacctc tgagaccgac acggtgcaag ccctggggt    6240 acaaagataa aagccagag tcctccccat caaggcgcca cgggccctgt aaacacataa     6300
accgaggaca cactgcatga gagatcacca ataaacgatg tagccataca gtgcacaaac    6360
tgctcactca gtatgtgcta gaaaatagcc ccagaaggca aggctcaaga ggggaaatac    6420
agttaggaat gtggcaggct tctagcccgg gctctgccag tcctggctct gaactgcggt    6480
tttctcaacc ttgagatccc ttgtgtgctt ttagtatgct gaaggatcac tcacttcaga    6540
atgctagtga aaatacagat tcccaagtcc gaccccactg aatcacaatg gctggaggtc    6600
attcggggcc ccgaatctgc attttcaccc ccacccaccc cccgggcagc tttaatgttg    6660
gcaggctagg aaccacagtt cggattactg cttaacaggg agataataac ctgcttcaga    6720
cgagctaggt cagacgagca attcaagagc taacaaggca acatgcgcca aaagccttgt    6780
aaacctcagg gcagtacaat tctttgcaaa taatagtaat tcaatcatgc aaataataat    6840
aatagtaaac gaactggaga gcgcactgga aacgccgcat agtccagctg agtcggtgcc    6900
accgccccat ccactccagc gcagagggac tgtctcttta aggccccccc acctccccaa    6960
ccgcgtcgct tctcccttgg gtacctggcc cggccgcgg cgcgtgcgtg cagggcctcc     7020
cggcggggcg gtcgcggcgg cgcgacgccg gcgccgttgc gtgcgcgcct ggccctgccc    7080
cttccccgcc ccttccccgc ccctcccct ccgcggggcc tccccgccc gcgcggtaca      7140 gctgggtcag tgacgcgggc gctgcagccg tcgctaccgc cgcgttctat tctccgaagc    7200
cggcgaccgc cccacctcct ccctccctcc cgcccgcttc ctctgcccac agcgccggcc    7260
agagcgagct agacaagggc acgcggggcc tcgcctagac ccgagaagac tgcgggcgcg    7320 cgcaagcgg ggcgtggaag ctgtgagcgc ccccatcccg gaggtctccg ccggctcccg     7380
ggtgagttgt caccgcggcc cggggcggc ggggccggca ttgtgccatc gacgcgctcg     7440
gccggctgtc aggggcgcgg gaccagcgcg caccgcccag gagtgacgct ggccggagcc    7500
cgggccggct tcggcggctc cccgcgcttc tctgcgccgg cccgctgtca cccggccgcg    7560
```

```
agccgcgccg ctgggagccc cgcgctggcg tggcgcggcc agccggccag cagtgggggt    7620
gcgcggccgg ggggaccggc ggctggtttg cggccgggaa cttggtgacc cgcggtccgg    7680
ggcgcgccgt cccgcgtcgc tgcccgggca gcaccggaag agccagacgc cgtgccgatg    7740
ggtgcagagg aggtaggcag aggccctctg tgccactgtc attactgccc tcagcccagc    7800
aaagctgcgg ggcttgcgct ggggcagggc tggcttagag aaggtggatt tcctgaggaa    7860
atctcagagc ccgcctgtgc gcaccgcggc attcgggagc ccccgcgcct cggctgctct    7920
ttaatctcaa aaacttctct tattaaccag gctaaactcc ccgaaaccag ctattttctt    7980
tcaaaaagta ggcacgtaca tacagacttt cctttttttcg cttggttttg agaccccagc    8040
tatgagtgtg gatctgactc tccctcatgg gagtcgtggc tggggagctg ctgaagtgga    8100
gaaaagttac cctggacgaa tttaggagca ggaggggggag gtggttatgg ggacagcaag    8160
acccaggagc aaagaggcgt caaaataaag tcttgggctg gttaaaggga agttggcgtc    8220
tgggcaagga ggcctaaagc tgttgttccc acagaatttt ctttcagtgg caggcgacat    8280
gctgggcttt gttgctctcg ctaactgggc tcctgtgtgc tcttccagag gtgcagtaag    8340
attactcagt tcaattaggc ctagggattt actccctttt ttgatctaca gagatgggaa    8400
gtatgtcttt ccttcacagt agttaattca tttcttgctg ttttcgttcc tctggtgtaa    8460
aaacatacat aggagttacg cacacacacc ttttctgttt tgggaattcc acacccaaac    8520
tgtcaccatc tagtggaggc tagtagagac atgtgcttgg cactgacttc tgagttctct    8580
gggttttgtg tttttagcta gaagcatatt caaccagaaa ttaaaatttt cctggagttg    8640
ggggaggtat gtctacatct caggaaagaa ggtatttaag cagcaataat atggaaaggt    8700
tcttgaggac ttactgagta ccaacctttg tgctaagggc tttacttttt tgaactcatt    8760
taataacaga cttttgatgt agatattatt atccccattc ttctagttga gacccaaacc    8820
aaacaagtta ataactcgcc catgtcaca  taggtatctc atggtggagc ccacagtctg    8880
aactactaga ttatactgct agtttctggt ttgtttacct tttgataaaa ttgaacctgg    8940
agtctttcta aaaccttctg aaagcactgc tgcttcaggc tgtttctcag atcatgagca    9000
ttctaaactc tttctcctgg gtacacactt acggtatgtt tgcataagat tcatttgttc    9060
attctttcat tcagtactcc caagtagtta tgtgataccg aatgtatgcc aggcactgtg    9120
ctaggtattg caggtactgc attgaataag tcagaatcca gctctcatgg actcacagcc    9180
tttaagtcca tttgttttgg tttatgttgt tagctttcat tgctggccat ttgctgctga    9240
aggaacttct gcccagcgag ttaaacagag gacagtattg gtatgagtcc tgatagatag    9300
gacttcctgt ctgcagagta atttttttgga tactgtagta gaaatggcat atgaaacaaa    9360
tcctcactta cacctagata gagacaggtg ccagggtgct cagtgtttaa accctgagag    9420
caaacccact gtcaaatggg caagtttgac ttctttcgct gaagcctgcc ttctgaaagc    9480
ccagaatttg gtgagataga agagaaagaa gggtagaatg aggtgttaca gatacaggct    9540
ggcagataaa gagacctcag cactttgtct gttttcctgg tcagtctctg aggtgtggtg    9600
attgaacttg tgttctttttt tatttttttat ttttttttgag atggagtctc gctctgtcac    9660
ccgggctgga gtgcagtggc acgatctcgg ctcactgcaa ccttcacctc ccaggttcaa    9720
acgattctct gcctcagcct cctgagcagc tgggactaca ggtgcgtgtc atcacgcctg    9780
gctaatttttt gtatttttag tagagacttg gttttaccat gttggctagg ctggtctcga    9840
acgcctgacc tcaggtgatc tgcccgtctt ggcctcccaa agtgttggga ttacgggcgt    9900
```

-continued

| | | |
|---|---|---|
| gagccaccgt gcccggcctg aacttgtgtt cttatgtaat gttgcatctc tcagtagggg | 9960 |
| atgtcctcct ttgctctttt ggtggggcag caattcctgc agcagccttc cctctacatg | 10020 |
| cacacacaca ccccttccaa aaggtaataa ttcacctggt ttctttaaag ttagaacttc | 10080 |
| tttcaagttt attgctacta agcattgttt cactccctcc acacttgtcc atttcccaca | 10140 |
| taaaaacttg gcttttgctt caaatatttt cttctgccct tttttcatat ccttagctct | 10200 |
| tctgacaacc aagttactac tggtatcatt tgtaggctgg gagaaataca gcatctttaa | 10260 |
| aaaaaaatag tgaggtacat actcttcctc atttcagtac caaacaagtg aactgtggag | 10320 |
| aatgaagcag aaccacttgc cagcagagag ggaaggccag agggcacacg tggttgtctt | 10380 |
| tcccctctag ttccccattt attaagagac aattcacact gcaggcccg aatgtcagca | 10440 |
| gatccattgg gcccaggttg tgtaattgcc atacatgaag tgagttatta agctcctgaa | 10500 |
| atgacatgct atctcctagt tgaagctgac aagcaggatt tattttccct cttctttctg | 10560 |
| tctggacact atggaagtct tgttagaggg tgttcgctca agcagtggga gaaagatcag | 10620 |
| aaggagccaa tagaggaggg agccccatgt cttgtcttct tttcaacttt gagagcaaac | 10680 |
| attgctttgt tgcagacttg aatgttgagg attaggacat ttggttaaat gtaag | 10735 |

<210> SEQ ID NO 6
<211> LENGTH: 3761
<212> TYPE: DNA
<213> ORGANISM: Homo sapiens

<400> SEQUENCE: 6

| | | |
|---|---|---|
| ccttgggtac ctggcccggc cggcggcgcg tgcgtgcagg gcctcccggc ggggcggtcg | 60 |
| cggcggcgcg acgccggcgc cgttgcgtgc gcgcctggcc ctgccccttt cccgcccctt | 120 |
| ccccgccccc tcccctccgc ggggcctccc ccgcccgcgc ggtacagctg ggtcagtgac | 180 |
| gcggcgctg cagccgtcgc taccgccgcg ttctattctc cgaagccggc gaccgcccca | 240 |
| cctcctccct ccctcccgcc cgcttcctct gcccacagcg ccggccagag cgagctagac | 300 |
| aagggcacgc ggggcctcgc ctagacccga gaagactgcg ggcgcgcgca agcggcggcg | 360 |
| tggaagctgt gagcgccccc atcccggagg tctccgccgg ctcccgggtg agttgtcacc | 420 |
| gcggcccggg ggcggcgggg ccggcattgt gccatcgacg cgctcggccg gctgtcaggg | 480 |
| gcgcgggacc agcgcgcacc gcccaggagt gacgctggcc ggagcccggg ccggcttcgg | 540 |
| cggctccccg cgcttctctg cgccggcccg ctgtcacccg gccgcgagcc gcgccgctgg | 600 |
| gagccccgcg ctggcgtggc gcggccagcc ggccagcagt gggggtgcgc ggccgggggg | 660 |
| accggcggct ggtttgcggc cgggaacttg gtgaccgcg gtccggggcg cgccgtcccg | 720 |
| cgtcgctgcc cgggcagcac cggaagagcc agacgccgtg ccgatgggtg cagaggaggt | 780 |
| aggcagaggc cctctgtgcc actgtcatta ctgccctcag cccagcaaag ctgcggggct | 840 |
| tgcgctgggg cagggctggc ttagagaagg tggatttcct gaggaaatct cagagcccgc | 900 |
| ctgtgcgcac cgcggcattc gggagccccc gcgcctcggc tgctctttaa tctcaaaaac | 960 |
| ttctcttatt aaccaggcta aactcccga aaccagctat tttctttcaa aaagtaggca | 1020 |
| cgtacataca gactttcctt ttttcgcttg gttttgagac cccagctatg agtgtggatc | 1080 |
| tgactctccc tcatgggagt cgtggctggg agctgctga agtggagaaa agttaccctg | 1140 |
| gacgaattta ggagcaggag ggggaggtgg ttatggggac agcaagaccc aggagcaaag | 1200 |
| aggcgtcaaa ataaagtctt gggctggtta aaggggaagtt ggcgtctggg caaggaggcc | 1260 |
| taaagctgtt gttcccacag aattttcttt cagtggcagg cgacatgctg ggctttgttg | 1320 |

-continued

```
ctctcgctaa ctgggctcct gtgtgctctt ccagaggtgc agtaagatta ctcagttcaa    1380
ttaggcctag ggatttactc ccttttttga tctacagaga tgggaagtat gtctttcctt    1440
cacagtagtt aattcatttc ttgctgtttt cgttcctctg gtgtaaaaac atacatagga    1500
gttacgcaca cacaccttt ctgttttggg aattccacac ccaaactgtc accatctagt     1560
ggaggctagt agagacatgt gcttggcact gacttctgag ttctctgggt tttgtgtttt    1620
tagctagaag catattcaac cagaaattaa aattttcctg gagttggggg aggtatgtct    1680
acatctcagg aaagaaggta tttaagcagc aataatatgg aaaggttctt gaggacttac    1740
tgagtaccaa cctttgtgct aagggcttta cttttttgaa ctcatttaat aacagacttt    1800
tgatgtagat attattatcc ccattcttct agttgagacc caaaccaaac aagttaaata    1860
actcgcccat gtcacatagg tatctcatgg tggagcccac agtctgaact actagattat    1920
actgctagtt tctggtttgt ttaccttttg ataaaattga acctggagtc tttctaaaac    1980
cttctgaaag cactgctgct tcaggctgtt tctcagatca tgagcattct aaactctttc    2040
tcctgggtac acacttacgg tatgtttgca taagattcat ttgttcattc tttcattcag    2100
tactcccaag tagttatgtg ataccgaatg tatgccaggc actgtgctag gtattgcagg    2160
tactgcattg aataagtcag aatccagctc tcatgactc acagccttta agtccatttg     2220
ttttggttta tgttgttagc tttcattgct ggccatttgc tgctgaagga acttctgccc    2280
agcgagttaa acagaggaca gtattggtat gagtcctgat agataggact tcctgtctgc    2340
agagtaattt tttggatact gtagtagaaa tggcatatga acaaatcct cacttacacc     2400 tagatagaga caggtgccag ggtgctcagt gtttaaaccc tgagagcaaa cccactgtca    2460
aatgggcaag tttgacttct ttcgctgaag cctgccttct gaaagcccag aatttggtga    2520
gatagaagag aaagaagggt agaatgaggt gttacagata caggctggca gataaagaga    2580
cctcagcact ttgtctgttt tcctggtcag tctctgaggt gtggtgattg aacttgtgtt    2640
cttttttatt ttttatttt tttgagatgg agtctcgctc tgtcacccgg gctggagtgc     2700
agtggcacga tctcggctca ctgcaacctt cacctcccag gttcaaacga ttctctgcct    2760
cagcctcctg agcagctggg actacaggtg cgtgtcatca cgcctggcta attttgtat     2820 ttttagtaga gacttggttt taccatgttg gctaggctgg tctcgaacgc ctgacctcag    2880
gtgatctgcc cgtcttggcc tcccaaagtg ttgggattac gggcgtgagc caccgtgccc    2940
ggcctgaact tgtgttctta tgtaatgttg catctctcag taggggatgt cctccttgc     3000 tcttttggtg gggcagcaat tcctgcagca gccttccctc tacatgcaca cacacacccc    3060
ttccaaaagg taataattca cctggtttct ttaaagttag aacttctttc aagtttattg    3120
ctactaagca ttgtttcact ccctccacac ttgtccattt cccacataaa aacttggctt    3180
ttgcttcaaa tattttcttc tgccctttt tcatatcctt agctcttctg acaaccaagt     3240
tactactggt atcatttgta ggctgggaga aatacagcat ctttaaaaaa aaatagtgag    3300
gtacatactc ttcctcattt cagtaccaaa caagtgaact gtggagaatg aagcagaacc    3360
acttgccagc agagagggaa ggccagaggg cacacgtggt tgtctttccc ctctagttcc    3420
ccatttatta agagacaatt cacacttgca ggcccgaatg tcagcagatc cattgggccc    3480
aggttgtgta attgccatac atgaagtgag ttattaagct cctgaaatga catgctatct    3540
cctagttgaa gctgacaagc aggatttatt ttccctcttc tttctgtctg gacactatgg    3600
aagtcttgtt agagggtgtt cgctcaagca gtgggagaaa gatcagaagg agccaataga    3660
```

-continued

```
ggagggagcc ccatgtcttg tcttcttttc aactttgaga gcaaacattg ctttgttgca      3720
gacttgaatg ttgaggatta ggacatttgg ttaaatgtaa g                          3761
```

<210> SEQ ID NO 7
<211> LENGTH: 909
<212> TYPE: DNA
<213> ORGANISM: Mus musculus

<400> SEQUENCE: 7

```
atgtgccatg gcaggatagc accaaagagc agctcagagt ttgttgtgac ttctgtgggg        60
catggagtgt tcttcaact ggtgatcctt tgcgctctgc tgggagatgg attagcctct        120
gtgtgtcctc tgcccccaga gccagagaat ggtggctaca tttgccaccc ccggccttgt       180
aaagacccct tgacaacagg cagtgtcatc gagtacctgt gtgcagaagg ctacatgttg       240
aagggtgact acaaatacct gacctgcaaa atggcgagt ggacgccagc catggaggtt       300
agctgtcatc tcattgaaga caaagaaacc catgcacttg gggtccctgc gctgtccata       360
gtggcttcca ctgccagctc tgtggcactc attctcctcc tcgtggtgct gtttgtactg       420
ctgcagccaa agctgaagtc tttccatcat agcaggcgtg aacagggggt ttctggggat       480
caagtctcca ttatggtgga tggtgtccag gttgcactac cttcacatga ggaagctgtg       540 tatgaagtt ctggtcactg catgccacca gctgatccca gagtacagat tgttctgtcg       600
gaagggtctg cacctagtgg gaggaacatg ccaagggaac agcagctgca aggtcaggag       660
gcctgctctt ctgcaggtgg agaggacgag gccccgggcc attctgggct gtgtgaagcc       720
tggggttccc agggctcaga gactgtgatg gtgcatcagg caaccacatc ttcctgggtg       780
gccggctcag ggagcagccg gccgacacac aaagacactg cagattcaga aaacagtgac       840
atacaaagcc ttttatccct gacatcacag gagtacacag atgatatccc actgttgaaa       900
gaagcatga                                                              909
```

<210> SEQ ID NO 8
<211> LENGTH: 302
<212> TYPE: PRT
<213> ORGANISM: Mus musculus

<400> SEQUENCE: 8

```
Met Cys His Gly Arg Ile Ala Pro Lys Ser Ser Glu Phe Val Val
1               5                   10                  15

Thr Ser Val Gly His Gly Val Phe Leu Gln Leu Val Ile Leu Cys Ala
                20                  25                  30

Leu Leu Gly Asp Gly Leu Ala Ser Val Cys Pro Leu Pro Pro Glu Pro
            35                  40                  45

Glu Asn Gly Gly Tyr Ile Cys His Pro Arg Pro Cys Lys Asp Pro Leu
        50                  55                  60

Thr Thr Gly Ser Val Ile Glu Tyr Leu Cys Ala Glu Gly Tyr Met Leu
    65                  70                  75                  80

Lys Gly Asp Tyr Lys Tyr Leu Thr Cys Lys Asn Gly Glu Trp Thr Pro
                85                  90                  95

Ala Met Glu Val Ser Cys His Leu Ile Glu Asp Lys Glu Thr His Ala
            100                 105                 110

Leu Gly Val Pro Ala Leu Ser Ile Val Ala Ser Thr Ser Ser Val
        115                 120                 125

Ala Leu Ile Leu Leu Leu Val Val Leu Phe Val Leu Leu Gln Pro Lys
    130                 135                 140
```

-continued

| | | | | | | | | | | | | | | |
|---|---|---|---|---|---|---|---|---|---|---|---|---|---|---|
| Leu | Lys | Ser | Phe | His | His | Ser | Arg | Arg | Glu | Gln | Gly | Val | Ser | Gly | Asp |
| 145 | | | | | 150 | | | | | 155 | | | | | 160 |
| Gln | Val | Ser | Ile | Met | Val | Asp | Gly | Val | Gln | Val | Ala | Leu | Pro | Ser | His |
| | | | | 165 | | | | | 170 | | | | | 175 | |
| Glu | Glu | Ala | Val | Tyr | Gly | Ser | Ser | Gly | His | Cys | Met | Pro | Pro | Ala | Asp |
| | | | 180 | | | | | 185 | | | | | 190 | | |
| Pro | Arg | Val | Gln | Ile | Val | Leu | Ser | Glu | Gly | Ser | Ala | Pro | Ser | Gly | Arg |
| | | 195 | | | | | 200 | | | | | 205 | | | |
| Asn | Met | Pro | Arg | Glu | Gln | Gln | Leu | Gln | Gly | Gln | Glu | Ala | Cys | Ser | Ser |
| | 210 | | | | | 215 | | | | | 220 | | | | |
| Ala | Gly | Gly | Glu | Asp | Glu | Ala | Pro | Gly | His | Ser | Gly | Leu | Cys | Glu | Ala |
| 225 | | | | | 230 | | | | | 235 | | | | | 240 |
| Trp | Gly | Ser | Gln | Gly | Ser | Glu | Thr | Val | Met | Val | His | Gln | Ala | Thr | Thr |
| | | | | 245 | | | | | 250 | | | | | 255 | |
| Ser | Ser | Trp | Val | Ala | Gly | Ser | Gly | Ser | Ser | Arg | Pro | Thr | His | Lys | Asp |
| | | | 260 | | | | | 265 | | | | | 270 | | |
| Thr | Ala | Asp | Ser | Glu | Asn | Ser | Asp | Ile | Gln | Ser | Leu | Leu | Ser | Leu | Thr |
| | | 275 | | | | | 280 | | | | | 285 | | | |
| Ser | Gln | Glu | Tyr | Thr | Asp | Asp | Ile | Pro | Leu | Leu | Lys | Glu | Ala | | |
| | 290 | | | | | 295 | | | | | 300 | | | | |

<210> SEQ ID NO 9
<211> LENGTH: 2464
<212> TYPE: DNA
<213> ORGANISM: Homo sapiens

<400> SEQUENCE: 9

```
tcgaggaatt taggagcagg aggggaggt ggttatgggg acagcaagac ccaggagcaa      60
agaggcgtca aaataaagtc ttgggctggt taaagggaag ttggcgtctg ggcaaggagg    120
cctaaagctg ttgttcccac agaatttcct ttcagtggca ggcgacatgc tgggctttgt    180
tgctctcgct aactgggctc ctgtgtgctc ttccagaggt gcagtaagat tactcagttc    240
aattaggcct agggatttac tccctttttt gatctacaga gatgggaagt atgtcttttcc   300
ttcacagtag ttaattcatt tcttgctgtt ttcgttcctc tggtgtaaaa acatacatag    360
gagttacgca cacacacctt ttctgttttg ggaattccac acccaaactg tcaccatcta    420
gtggaggcta gtagagacat gtgcttggca ctgacttctg agttctctgg gttttgtgtt    480
tttagctaga agcatattca accagaaatt aaaattttcc tggagttggg ggaggtatgt    540
ctacatctca ggaagaagg tatttaagca gcaataatat ggaaaggttc ttgaggactt     600
actgagtacc aacctttgtg ctaagggctt tacttttttg aactcattta ataacagact    660
tttgatgtag atattattat ccccattctt ctagttgaga cccaaaccaa acaagttaaa    720
taactcgccc atgtcacata ggtatctcat ggtggagccc acagtctgaa ctactagatt    780
atactgctag tttctggttt gtttaccttt tgataaaatt gaacctggag tcttttctaaa   840
accttctgaa agcactgctg cttcaggctg tttctcagat catgagcatt ctaaactctt    900
tctcctgggt acacacttac ggtatgtttg cataagattc atttgttcat tctttcattc    960
agtactccca gtagttatg tgataccgaa tgtatgccag gcactgtgct aggtattgca    1020
ggtactgcat tgaataagtc agaatccagc tctcatggac tcacagcctt taagtccatt   1080
tgttttggtt tatgttgtta gctttcattg ctggccattt gctgctgaag gaacttctgc   1140
ccagcgagtt aaacagagga cagtattggt atgagtcctg atagatagga cttcctgtct   1200
gcagagtaat tttttggata ctgtagtaga aatggcatat gaaacaaatc ctcacttaca   1260
```

-continued

```
cctagataga gacaggtgcc agggtgctca gtgtttaaac cctgagagca aacccactgt    1320
caaatgggca agtttgactt ctttcgctga agcctgcctt ctgaaagccc agaatttggt    1380
gagatagaag agaagaagg gtagaatgag gtgttacaga tacaggctgg cagataaaga    1440
gacctcagca ctttgtctgt tttcctggtc agtctctgag gtgtggtgat tgaacttgtg    1500
ttctttttta tttttattt ttttttgagat ggagtctcgc tctgtcaccc gggctggagt    1560
gcagtggcac gatctcggct cactgcaacc ttcacctccc aggttcaaac gattctctgc    1620
ctcagcctcc tgagcagctg ggactacagg tgcgtgtcat cacgcctggc taattttgt    1680
attttagta gagacttggt tttaccatgt tggctaggct ggtctcgaac gcctgacctc    1740
aggtgatctg cccgtcttgg cctcccaaag tgttgggatt acgggcgtga gccaccgtgc    1800
ccggcctgaa cttgtgttct tatgtaatgt tgcatctctc agtaggggat gtcctccttt    1860
gctcttttgg tggggcagca attcctgcag cagccttccc tctacatgca cacacacacc    1920
ccttccaaaa ggtaataatt cacctggttt ctttaaagtt agaacttctt tcaagtttat    1980
tgctactaag cattgtttca ctccctccac acttgtccat ttcccacata aaaacttggc    2040
ttttgcttca aatattttct tctgcccttt tttcatatcc ttagctcttc tgacaaccaa    2100
gttactactg gtatcatttg taggctggga gaaatacagc atctttaaaa aaaaatagtg    2160
aggtacatac tcttcctcat ttcagtacca aacaagtgaa ctgtggagaa tgaagcagaa    2220
ccacttgcca gcagagaggg aaggccagag ggcacacgtg gttgtctttc ccctctagtt    2280
ccccatttat taagagacaa ttcacacttg caggcccgaa tgtcagcaga tccattgggc    2340
ccaggttgtg taattgccat acatgaagtg agttattaag ctcctgaaat gacatgctat    2400
ctcctagttg aagctgacaa gcaggattta ttttccctct ctttctgtc tggacactat    2460
ggaa                                                                 2464
```

<210> SEQ ID NO 10
<211> LENGTH: 914
<212> TYPE: DNA
<213> ORGANISM: Homo sapiens

<400> SEQUENCE: 10

```
gggctggagt gcagtggcac gatctcggct cactgcaacc ttcacctccc aggttcaaac     60
gattctctgc ctcagcctcc tgagcagctg ggactacagg tgcgtgtcat cacgcctggc    120
taattttgt attttagta gagacttggt tttaccatgt tggctaggct ggtctcgaac    180
gcctgacctc aggtgatctg cccgtcttgg cctcccaaag tgttgggatt acgggcgtga    240
gccaccgtgc ccggcctgaa cttgtgttct tatgtaatgt tgcatctctc agtaggggat    300
gtcctccttt gctcttttgg tggggcagca attcctgcag cagccttccc tctacatgca    360
cacacacacc ccttccaaaa ggtaataatt cacctggttt ctttaaagtt agaacttctt    420
tcaagtttat tgctactaag cattgtttca ctccctccac acttgtccat ttcccacata    480
aaaacttggc ttttgcttca aatattttct tctgcccttt tttcatatcc ttagctcttc    540
tgacaaccaa gttactactg gtatcatttg taggctggga gaaatacagc atctttaaaa    600
aaaaatagtg aggtacatac tcttcctcat ttcagtacca aacaagtgaa ctgtggagaa    660
tgaagcagaa ccacttgcca gcagagaggg aaggccagag ggcacacgtg gttgtctttc    720
ccctctagtt ccccatttat taagagacaa ttcacacttg caggcccgaa tgtcagcaga    780
tccattgggc ccaggttgtg taattgccat acatgaagtg agttattaag ctcctgaaat    840
```

```
gacatgctat ctcctagttg aagctgacaa gcaggattta ttttccctct tctttctgtc    900
tggacactat ggaa                                                      914

<210> SEQ ID NO 11
<211> LENGTH: 1203
<212> TYPE: DNA
<213> ORGANISM: Homo sapiens

<400> SEQUENCE: 11
tcgaggaatt taggagcagg agggggaggt ggttatgggg acagcaagac ccaggagcaa     60
agaggcgtca aaataaagtc ttgggctggt taaaggaag ttggcgtctg ggcaaggagg    120
cctaaagctg ttgttcccac agaattttct ttcagtggca ggcgacatgc tgggctttgt    180
tgctctcgct aactgggctc ctgtgtgctc ttccagagt gcagtaagat tactcagttc    240
aattaggcct agggatttac tccctttttt gatctacaga gatgggaagt atgtctttcc    300
ttcacagtag ttaattcatt tcttgctgtt ttcgttcctc tggtgtaaaa acatacatag    360
gagttacgca cacacacctt ttctgttttg ggaattccac acccaaactg tcaccatcta    420
gtggaggcta gtagagacat gtgcttggca ctgacttctg agttctctgg gttttgtgtt    480
tttagctaga agcatattca accagaaatt aaaattttcc tggagttggg ggagtatgt     540 ctacatctca ggaagaagg tatttaagca gcaataatat ggaaaggttc ttgaggactt    600
actgagtacc aacctttgtg ctaagggctt acttttttg aactcattta ataacagact    660
tttgatgtag atattattat ccccattctt ctagttgaga cccaaaccaa acaagttaaa    720
taactcgccc atgtcacata ggtatctcat ggtggagccc acagtctgaa ctactagatt    780
atactgctag tttctggttt gtttaccttt tgataaaatt gaacctggag tctttctaaa    840
accttctgaa agcactgctg cttcaggctg tttctcagat catgagcatt ctaaactctt    900
tctcctgggt acacacttac ggtatgtttg cataagattc atttgttcat tctttcattc    960
agtactccca gtagttatg tgataccgaa tgtatgccag gcactgtgct aggtattgca   1020
ggtactgcat tgaataagtc agaatccagc tctcatggac tcacagcctt taagtccatt   1080
tgttttggtt tatgttgtta gctttcattg ctggccattt gctgctgaag gaacttctgc   1140
ccagcgagtt aaacagagga cagtattggt atgagtcctg atagatagga cttcctgtct   1200
gca                                                                 1203

<210> SEQ ID NO 12
<211> LENGTH: 575
<212> TYPE: DNA
<213> ORGANISM: Homo sapiens

<400> SEQUENCE: 12
gcagccttcc ctctacatgc acacacacac cccttccaaa aggtaataat tcacctggtt     60
tctttaaagt tagaacttct ttcaagtttta ttgctactaa gcattgtttc actccctcca    120
cacttgtcca ttttcccacat aaaaacttgg cttttgcttc aaatattttc ttctgcccttt   180 ttttcatatc cttagctctt ctgacaacca agttactact ggtatcattt gtaggctggg    240
agaaatacag catcttttaaa aaaaaatagt gaggtacata ctcttcctca tttcagtacc    300
aaacaagtga actgtggaga atgaagcaga accacttgcc agcagagagg gaaggccaga    360
gggcacacgt ggttgtcttt cccctctagt tccccattta ttaagagaca attcacactt    420
gcaggcccga atgtcagcag atccattggg cccaggttgt gtaattgcca tacatgaagt    480
gagttattaa gctcctgaaa tgacatgcta tctcctagtt gaagctgaca agcaggattt    540
```

```
attttccctc ttctttctgt ctggacacta tggaa                              575
```

```
<210> SEQ ID NO 13
<211> LENGTH: 1203
<212> TYPE: DNA
<213> ORGANISM: Homo sapiens

<400> SEQUENCE: 13
tcgaggaatt taggagcagg agggggaggt ggttatgggg acagcaagac ccaggagcaa    60
agaggcgtca aaataaagtc ttgggctggt taaagggaag ttggcgtctg ggcaaggagg   120
cctaaagctg ttgttcccac agaattttct ttcagtggca ggcgacatgc tgggctttgt   180
tgctctcgct aactgggctc ctgtgtgctc ttccagaggt gcagtaagat tactcagttc   240
aattaggcct agggatttac tcccttttt  gatctacaga gatgggaagt atgtctttcc   300
ttcacagtag ttaattcatt tcttgctgtt ttcgttcctc tggtgtaaaa acatacatag   360
gagttacgca cacacacctt ttctgttttg ggaattccac acccaaactg tcaccatcta   420
gtggaggcta gtagagacat gtgcttggca ctgacttctg agttctctgg gttttgtgtt   480
tttagctaga agcatattca accagaaatt aaaattttcc tggagttggg ggaggtatgt   540
ctacatctca ggaagaagg  tatttaagca gcaataatat ggaaaggttc ttgaggactt   600
actgagtacc aaccttgtg  ctaagggctt tacttttttg aactcattta ataacagact   660
tttgatgtag atattattat ccccattctt ctagttgaga cccaaaccaa acaagttaaa   720
taactcgccc atgtcacata ggtatctcat ggtggagccc acagtctgaa ctactagatt   780
atactgctag tttctggttt gtttaccttt tgataaaatt gaacctggag tctttctaaa   840
accttctgaa agcactgctg cttcaggctg tttctcagat catgagcatt ctaaactctt   900
tctcctgggt acacacttac ggtatgtttg cataagattc atttgttcat tctttcattc   960
agtactccca gtagttatg  tgataccgaa tgtatgccag gcactgtgct aggtattgca  1020
ggtactgcat tgaataagtc agaatccagc tctcatggac tcacagcctt taagtccatt  1080
tgttttggtt tatgttgtta gctttcattg ctggccattt gctgctgaag gaacttctgc  1140
ccagcgagtt aaacagagga cagtattggt atgagtcctg atagatagga cttcctgtct  1200
gca                                                               1203
```

```
<210> SEQ ID NO 14
<211> LENGTH: 1637
<212> TYPE: DNA
<213> ORGANISM: Homo sapiens

<400> SEQUENCE: 14
tcgaggaatt taggagcagg agggggaggt ggttatgggg acagcaagac ccaggagcaa    60
agaggcgtca aaataaagtc ttgggctggt taaagggaag ttggcgtctg ggcaaggagg   120
cctaaagctg ttgttcccac agaattttct ttcagtggca ggcgacatgc tgggctttgt   180
tgctctcgct aactgggctc ctgtgtgctc ttccagaggt gcagtaagat tactcagttc   240
aattaggcct agggatttac tcccttttt  gatctacaga gatgggaagt atgtctttcc   300
ttcacagtag ttaattcatt tcttgctgtt ttcgttcctc tggtgtaaaa acatacatag   360
gagttacgca cacacacctt ttctgttttg ggaattccac acccaaactg tcaccatcta   420
gtggaggcta gtagagacat gtgcttggca ctgacttctg agttctctgg gttttgtgtt   480
tttagctaga agcatattca accagaaatt aaaattttcc tggagttggg ggaggtatgt   540
```

```
ctacatctca ggaaagaagg tatttaagca gcaataatat ggaaaggttc ttgaggactt      600
actgagtacc aacctttgtg ctaagggctt tactttttg aactcattta ataacagact       660
tttgatgtag atattattat ccccattctt ctagttgaga cccaaaccaa acaagttaaa      720
taactcgccc atgtcacata gtatctcat ggtggagccc acagtctgaa ctactagatt      780
atactgctag tttctggttt gtttaccttt tgataaaatt gaacctggag tcttttctaaa    840 accttctgaa agcactgctg cttcaggctg tttctcagat catgagcatt ctaaactctt     900
tctcctgggt acacacttac ggtatgtttg cataagattc atttgttcat tctttcattc    960
agtactccca gtagttatg tgataccgaa tgtatgccag gcactgtgct aggtattgca      1020
ggtactgcat tgaataagtc agaatccagc tctcatggac tcacagcctt taagtccatt    1080
tgttttggtt tatgttgtta gctttcattg ctggccattt gctgctgaag gaacttctgc    1140
ccagcgagtt aaacagagga cagtattggt atgagtcctg atagatagga cttcctgtct    1200
gcagagtaat tttttggata ctgtagtaga aatggcatat gaaacaaatc ctcacttaca    1260
cctagataga gacaggtgcc agggtgctca gtgtttaaac cctgagagca acccactgt     1320 caaatgggca gtttgactt cttcgctga agcctgcctt ctgaaagccc agaatttggt       1380
gagatagaag agaaagaagg gtagaatgag gtgttacaga tacaggctgg cagataaaga    1440
gacctcagca ctttgtctgt tttcctggtc agtctgag gtgtggtgat tgaacttgtg       1500 ttcttttta ttttttattt ttttgagat ggagtctcgc tctgtcaccc gggctggagt       1560
gcagtggcac gatctcggct cactgcaacc ttcacctccc aggttcaaac gattctctgc    1620
ctcagcctcc tgagcag                                                    1637

<210> SEQ ID NO 15
<211> LENGTH: 577
<212> TYPE: DNA
<213> ORGANISM: Homo sapiens

<400> SEQUENCE: 15
cagcagcctt ccctctacat gcacacacac acccccttcca aaaggtaata attcacctgg    60
tttctttaaa gttagaactt cttcaagtt tattgctact aagcattgtt tcactccctc     120
cacacttgtc catttcccac ataaaaactt ggcttttgct tcaaatattt tcttctgccc    180
ttttttcata tccttagctc ttctgacaac caagttacta ctggtatcat ttgtaggctg   240
ggagaaatac agcatcttta aaaaaaaata gtgaggtaca tactcttcct catttcagta    300
ccaaacaagt gaactgtgga gaatgaagca gaaccacttg ccagcagaga gggaaggcca    360
gagggcacac gtggttgtct ttcccctcta gttccccatt tattaagaga caattcacac    420
ttgcaggccc gaatgtcagc agatccattg ggcccaggtt gtgtaattgc catacatgaa    480
gtgagttatt aagctcctga aatgacatgc tatctcctag ttgaagctga caagcaggat    540
ttattttccc tcttctttct gtctggacac tatggaa                             577

<210> SEQ ID NO 16
<211> LENGTH: 956
<212> TYPE: DNA
<213> ORGANISM: Homo sapiens

<400> SEQUENCE: 16
ggtacctggc ccggccggcg gcgcgtgcgt gcagggcctc ccggcggggc ggtcgcggcg     60
gcgcgacgcc ggcgcgttg cgtgcgcgcc tggccctgcc cctttcccgc ccttcccccg    120
cccctccccc tccgcggggc ctcccccgcc cgcgcggtac agctgggtca gtgacgcggg    180
```

```
cgctgcagcc gtcgctaccg ccgcgttcta ttctccgaag ccggcgaccg ccccacctcc      240
tccctccctc ccgcccgctt cctctgccca cagcgccggc cagagcgagc tagacaaggg      300
cacgcggggc ctcgcctaga cccgagaaga ctgcgggcgc gcgcaagcgg cggcgtggaa      360
gctgtgagcg cccccatccc ggaggtctcc gccggctccc gggtgagttg tcaccgcggc      420 ccggggggcgg cggggccggc attgtgccat cgacgcgctc ggccggctgt cagggcgcg      480 ggaccagcgc gcaccgccca ggagtgacgc tggccggagc ccgggccggc ttcggcggct      540
ccccgcgctt ctctgcgccg gcccgctgtc accggccgc gagccgcgcc gctgggagcc      600
ccgcgctggc gtggcgcggc cagccggcca gcagtggggg ctgcgcggcc gggggaccg      660 gcggctggtt tgcggccggg aacttggtga cccgcggtcc ggggcgcgcc gtcccgcgtc      720
gctgcccggg cagcaccgga agagccagac gccgtgccga tgggtgcaga ggaggtaggc      780
agaggccctc tgtgccactg tcattactgc cctcagccca gcaaagctgc ggggcttgcg      840
ctggggcagg gctggcttag agaaggtgga tttcctgagg aaatctcaga gcccgcctgt      900
gcgcaccgcg gcattcggga gccccgcgc ctcggctgct ctttaatctc aaaaac          956

<210> SEQ ID NO 17
<211> LENGTH: 26
<212> TYPE: DNA
<213> ORGANISM: Unknown
<220> FEATURE:
<223> OTHER INFORMATION: human or mouse

<400> SEQUENCE: 17
ctcgagtgcc atggcaggat agcacc                                            26

<210> SEQ ID NO 18
<211> LENGTH: 26
<212> TYPE: DNA
<213> ORGANISM: Unknown
<220> FEATURE:
<223> OTHER INFORMATION: human or mouse

<400> SEQUENCE: 18
tctagatcat gcttctttca acagtg                                            26

<210> SEQ ID NO 19
<211> LENGTH: 25
<212> TYPE: DNA
<213> ORGANISM: Homo sapiens

<400> SEQUENCE: 19
ctcgagtgca tggcaggata gcacc                                             25
```